US010214574B2

(12) United States Patent
Davis et al.

(10) Patent No.: US 10,214,574 B2
(45) Date of Patent: Feb. 26, 2019

(54) ENGINEERED CALMODULIN FOR TREATMENT OF RYANOPATHIES

(71) Applicant: Ohio State Innovation Foundation, Columbus, OH (US)

(72) Inventors: Jonathan Paul Davis, Westerville, OH (US); Sandor Gyorke, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/564,858

(22) PCT Filed: Apr. 15, 2016

(86) PCT No.: PCT/US2016/027889
§ 371 (c)(1),
(2) Date: Oct. 6, 2017

(87) PCT Pub. No.: WO2016/168694
PCT Pub. Date: Oct. 20, 2016

(65) Prior Publication Data
US 2018/0086803 A1    Mar. 29, 2018

Related U.S. Application Data

(60) Provisional application No. 62/147,903, filed on Apr. 15, 2015.

(51) Int. Cl.
*C07K 14/47*    (2006.01)
*A61K 38/17*    (2006.01)
*A61K 38/00*    (2006.01)
*C12N 15/861*   (2006.01)

(52) U.S. Cl.
CPC ...... *C07K 14/4728* (2013.01); *A61K 38/1738* (2013.01); *A61K 38/00* (2013.01); *C12N 15/861* (2013.01); *C12N 2750/14143* (2013.01)

(58) Field of Classification Search
CPC .................. C07K 14/4728; A61K 38/1738
See application file for complete search history.

(56) References Cited

U.S. PATENT DOCUMENTS

| 5,579,250 | A | 11/1996 | Balaji et al. |
| 5,612,895 | A | 3/1997 | Balaji et al. |
| 5,631,280 | A | 5/1997 | Ciccarone et al. |
| 2005/0079170 | A1 | 4/2005 | Le Gall et al. |
| 2005/0112574 | A1 | 5/2005 | Gamble et al. |
| 2007/0049572 | A1 | 3/2007 | Marks et al. |

FOREIGN PATENT DOCUMENTS

| CA | 2583716 A1 | 10/2008 |
| CA | 2782014 A1 | 6/2011 |

OTHER PUBLICATIONS

Balshaw, D. M., et al., Calmodulin binding and inhibition of cardiac muscle calcium release channel (ryanodine receptor), J Biol Chem 276:20144-20153, (2001).
Beard, N. A., et al., Regulation of ryanodine receptors by calsequestrin: effect of high luminal Ca2+ and phosphorylation, Biophys J 88:3444-3454, (2005).
Belevych, A. E., et al., Redox modification of ryanodine receptors underlies calcium alternans in a canine model of sudden cardiac death, Cardiovasc Res 84:387-395, (2009).
Belevych, A. E., et al., The relationship between arrhythmogenesis and impaired contractility in heart failure: role of altered ryanodine receptor function, Cardiovasc Res 90:493-502, (2011).
Belevych, A. E., et al., Shortened Ca2+ signaling refractoriness underlies cellular arrhythmogenesis in a postinfarction model of sudden cardiac death, Circ Res 110:569-577, (2012).
Belevych, A. E., et al., "Ryanopathy": causes and manifestations of RyR2 dysfunction in heart failure, Cardiovascular research 98:240-247, (2013).
Bers, D. M., Cardiac excitation-contraction coupling, Nature 415:198-205, (2002).
Black, D. J., et al., Acid pairs increase the N-terminal Ca2+ affinity of CaM by increasing the rate of Ca2+ association, Biochemistry 39:13831-13837, (2000).
Brunello, L., et al., Decreased RyR2 refractoriness determines myocardial synchronization of aberrant Ca2+ release in a genetic model of arrhythmia, Proc Natl Acad Sci USA 110:10312-10317, (2013).
Cerrone, M., et al., Arrhythmogenic mechanisms in a mouse model of catecholaminergic polymorphic ventricular tachycardia, Circ Res 101:1039-1048, (2007).
Chattopadhyaya, R., et al., Calmodulin structure refined at 1.7 A resolution, Journal of molecular biology 228:1177-1192, (1992).
Chin, D., et al. Calmodulin: a prototypical calcium sensor (2000) Trends Cell Biol 10:322-328.
Cho, M. J., et al. Reciprocal regulation of mammalian nitric oxide synthase and calcineurin by plant calmodulin isoforms, Biochemistry 37:15593-15597, (1998).
Curran, J., et al., EHD3-dependent endosome pathway regulates cardiac membrane excitability and physiology, Circ Res 115:68-78, (2014).
Denegri, M., et al., Viral gene transfer rescues arrhythmogenic phenotype and ultrastructural abnormalities in adult calsequestrin-null mice with inherited arrhythmias, Circ Res 110:663-668, (2012).

(Continued)

*Primary Examiner* — Antonio Galisteo Gonzalez
(74) *Attorney, Agent, or Firm* — Thomas|Horstemeyer, LLP

(57) ABSTRACT

Compositions and methods are disclosed for altering the binding affinity of calmodulin for ryanodine receptor 2 (RyR2). As disclosed herein, these therapeutic calmodulin (TCaM) proteins can be used to correct ryanopathies by prolonging the RyR2 refractory period. Therefore, also disclosed is a method for treating a ryanopathy-associated disease in a subject that involves administering to the subject a composition comprising a TCaM disclosed herein.

4 Claims, 19 Drawing Sheets
Specification includes a Sequence Listing.

(56) References Cited

OTHER PUBLICATIONS

Denegri, M., et al., Single delivery of an adeno-associated viral construct to transfer the CASQ2 gene to knock-in mice affected by catecholaminergic polymorphic ventricular tachycardia is able to cure the disease from birth to advanced age, Circulation 129:2673-2681, (2014).
Fabiato, A., Time and calcium dependence of activation and inactivation of calcium-induced release of calcium from the sarcoplasmic reticulum of a skinned canine cardiac Purkinje cell, J Gen Physiol 85:247-289, (1985).
Fukuda, M., et al., Enhanced binding of calmodulin to RyR2 corrects arrhythmogenic channel disorder in CPVT-associated myocytes, Biochem Biophys Res Commun 448:1-7, (2014).
Glynn, P., et al. Voltage-Gated Sodium Channel Phosphorylation at Ser571 Regulates Late Current, Arrhythmia, and Cardiac Function in Vivo(2015) Circulation 132:567-577.
Guo, T., et al., FRET detection of calmodulin binding to the cardiac RyR2 calcium release channel, Biophysical journal 101:2170-2177, (2011).
Gyorke, I., et al. The Role of Calsequestrin, Triadin, and Junctin in Conferring Cardiac Ryanodine Receptor Responsiveness to Luminal Calcium(2004) Biophys J 86:2121-2128.
Gyorke, S., et al. Modulation of ryanodine receptor by luminal calcium and accessory proteins in health and cardiac disease(2008) Cardiovascular research 77:245-255.
Hamamoto, T., et al., In situ Ca2+ dynamics of Purkinje fibers and its interconnection with subjacent ventricular myocytes, J Mol Cell Cardiol 38:561-569, (2005).
Herron, T. J., et al., Purkinje cell calcium dysregulation is the cellular mechanism that underlies catecholaminergic polymorphic ventricular tachycardia, Heart Rhythm 7:1122-1128, (2010).
Hund, T. J., et al. Role of activated CaMKII in abnormal calcium homeostasis and INa remodeling after myocardial Infarction: Insights from mathematical modeling(2008) J Mol Cell Cardiol 45:420-428.
Hwang, H. S., et al., Divergent regulation of ryanodine receptor 2 calcium release channels by arrhythmogenic human calmodulin missense mutants, Circ Res 114:1114-1124, (2014).
Johnson, P. R., et al., Vectormediated gene transfer engenders long-lived neutralizing activity and protection against SIV infection in monkeys, Nature medicine 15:901-906, (2009).
Jung, C. B., et al. Dantrolene rescues arrhythmogenic RYR2 defect in a patient-specific stem cell model of catecholaminergic polymorphic ventricular tachycardia(2012) EMBO Mol Med 4:180-191.
Kim, E. E Y. et al., Multiple Cterminal tail Ca(2+)/CaMs regulate Ca(V)1.2 function but do not mediate channel dimerization (2010) The EMBO journal 29:3924-3938.
Knollmann, B. C., et al., Casq2 deletion causes sarcoplasmic reticulum volume increase, premature Ca2+ release, and catecholaminergic polymorphic ventricular tachycardia, J Clin Invest 116:2510-2520, (2006).
Kobayashi, S., et al. Dantrolene, a Therapeutic Agent for Malignant Hyperthermia, Inhibits Catecholaminergic Polymorphic Ventricular Tachycardia in a RyR2R2474S/+ Knock-In Mouse Model(2010) Circ J 74:2579-2584.
Kondo, R., et al. A Point Mutation in a Plant Calmodulin Is Responsible for Its Inhibition of Nitric-oxide Synthase (1999) J Biol Chem 274:36213-36218.
Komyeyev, D., et al., Calsequestrin 2 deletion shortens the refractoriness of Ca2+ release and reduces rate-dependent Ca2+-alternans in intact mouse hearts, J Mol Cell Cardiol 52:21-31, (2012).
Kubalova, Z., et al., Modulation of cytosolic and intra-sarcoplasmic reticulum calcium waves by calsequestrin in rat cardiac myocytes, J Physiol 561:515-524, (2004).
Lee, S. H., et al., Differential regulation of Ca2+/calmodulindependent enzymes by plant calmodulin isoforms and free Ca2+ concentration, Biochem J 350 Pt 1:299-306, (2000).
Lehnart, S. E., et al. Stabilization of cardiac ryanodine receptor prevents intracellular calcium leak and arrhythmias (2006) Proc Natl Acad Sci USA 103:7906-7910.
Limpitikul, W. B., et al., Calmodulin mutations associated with long QT syndrome prevent inactivation of cardiac L-type Ca(2+) currents and promote proarrhythmic behavior in ventricular myocytes, J Mol Cell Cardiol 74:115-124, (2014).
Liu, Q., et al. Direct Interaction and Reciprocal Regulation between ASK1 and Calcineurin-NFAT Control Cardiomyocyte Death and Growth (2006) Mol Cell Biol 26:3785-3797.
Liu X et al., Role of Leaky Neuronal Ryanodine Receptors in Stress-Induced Cognitive Dysfunction(2012) Cell 150:1055-1067.
Liu B., et al., Engineered troponin C constructs correct diseaserelated cardiac myofilament calcium sensitivity, J Biol Chem 287:20027-20036, (2012).
Liu B. et al. Ablation of HRC alleviates cardiac arrhythmia and improves abnormal Ca handling in CASQ2 knockout mice prone to CPVT(2015) Cardiovasc Res 108:299-311.
Loaiza R. et al., Heterogeneity of ryanodine receptor dysfunction in a mouse model of catecholaminergic polymorphic ventricular tachycardia, Circ Res 112:298-308, (2013).
Lukyanenko, V., et al. Regulation of calcium release by calcium inside the sarcoplasmic reticulum in ventricular myocytes, Pflugers Arch 432:1047-1054, (1996).
Lukyanenko, V., et al., Dynamic regulation of sarcoplasmic reticulum Ca(2+) content and release by luminal Ca(2+)-sensitive leak in rat ventricular myocytes, Biophys J 81:785-798, (2001).
Maier, L. S., et al. Calcium, Calmodulin, and Calcium-Calmodulin Kinase II: Heartbeat to Heartbeat and Beyond(2002) J Mol Cell Cardiol 34:919-939.
Maximciuc, A. A., et al., Complex of calmodulin with a ryanodine receptor target reveals a novel, flexible binding mode, Structure 14:1547-1556, (2006).
Mishra, S., et al. Cardiac Hypertrophy and Heart Failure Development Through Gq and CaM Kinase II Signaling(2010) J Cardiovasc Pharmacol 56:598-603.
Nyegaard, M., et al., Mutations in calmodulin cause ventricular tachycardia and sudden cardiac death, American journal of human genetics 91:703-712, (2012).
Qian, Z., et al. Efficient Delivery of Cyclic Peptides into Mammalian Cells with Short Sequence Motifs(2013) ACS Chem Biol 8:423-431.
Qin, J., et al.,Luminal Ca2+ regulation of single cardiac ryanodine receptors: insights provided by calsequestrin and its mutants, J Gen Physiol 131:325-334, (2008).
Radwanski, P. B., et al., Store-dependent deactivation: Cooling the chain-reaction of myocardial calcium signaling, J Mol Cell Cardiol 58:77-83, (2013).
Radwanski, P. B., et al., Neuronal Na+ Channel Blockade Suppresses Arrhythmogenic Diastolic Ca2+ Release, Cardiovasc Res 106:143-152, (2014).
Ramay, H. R., et al., Recovery of cardiac calcium release is controlled by sarcoplasmic reticulum refilling and ryanodine receptor sensitivity, Cardiovasc Res 91:598-605, (2011).
Rizzi, N., et al. Unexpected Structural and Functional Consequences of the R33Q Homozygous Mutation in Cardiac Calsequestrin (2008) Circ Res 103:298-306.
Santulli G., et al. Essential Roles of Intracellular Calcium Release Channels in Muscle, Brain, Metabolism, and Aging (2015) Current Mol Pharmac 8:206-222.
Shettigar, V., et al. Rationally engineered Troponin C modulates in vivo cardiac function and performance in health and disease(2016) Nat Commun 7:10794.
Sorensen, A. B., et al. Calmodulin in a Heartbeat (2013) The FEBS journal 280:5511-5532.
Stevens, S. C., et al., Intra-sarcoplasmic reticulum Ca2+ oscillations are driven by dynamic regulation of ryanodine receptor function by luminal Ca2+ in cardiomyocytes, J Physiol 587:4863-4872, (2009).
Ter Keurs, H. E., et al. Calcium and Arrhythmogenesis (2007) Physiol Rev 87:457-506.

(56) References Cited

OTHER PUBLICATIONS

Terentyev, D., et al., Calsequestrin determines the functional size and stability of cardiac intracellular calcium stores: Mechanism for hereditary arrhythmia, Proc Natl Acad Sci USA 100:11759-11764, (2003).
Terentyev, D., et al., Triadin overexpression stimulates excitation-contraction coupling and increases predisposition to cellular arrhythmia in cardiac myocytes, Circulation research 96:651-658, (2005).
Terentyev, D., et al. Abnormal Interactions of Calsequestrin With the Ryanodine Receptor Calcium Release Channel Complex Linked to Exercise-Induced Sudden Cardiac Death(2006) Circ Res 98:1151-1158.
Terentyev, D., et al., Redox Modification of Ryanodine Receptors Contributes to Sarcoplasmic Reticulum Ca2+ Leak in Chronic Heart Failure, Circ Res 103:1466-1472, (2008).
Terentyev, D., et al., Modulation of SR Ca release by luminal Ca and calsequestrin in cardiac myocytes: effects of CASQ2 mutations linked to sudden cardiac death, Biophys J 95:2037-2048, (2008).
Tidow, H., et al., Structural diversity of calmodulin binding to its target sites,The FEBS journal 280:5551-5565, (2013).
Tikunova, S. B., et al., Effect of calcium-sensitizing mutations on calcium binding and exchange with troponin C in increasingly complex biochemical systems Biochemistry 49:1975-1984, (2010).
van der Werf, C., et al. Flecainide Therapy Reduces Exercise-Induced Ventricular Arrhythmias in Patients With Catecholaminergic Polymorphic Ventricular Tachycardia (2011) J Am Coll Cardiol 57:2244-2254.
Van Lierop, J. E., et al. Activation of smooth muscle myosin light chain kinase by calmodulin. Role of LYS(30) and GLY(40), J Biol Chem 277:6550-6558, (2002).
Venetucci, L., et al., Inherited Calcium Channelopathies in the Pathophysiology of Arrhythmias (2012) Nat Rev Cardiol 9:561-575.
Wang, H., et al. Phosphodiesterase 5 restricts NOS3/Soluble guanylate cyclase signaling to L-type Ca2+ current in cardiac myocytes (2009) J Mol Cell Cardiol 47:304-314.
Watanabe, H., et al. Flecainide prevents catecholaminergic polymorphic ventricular tachycardia in mice and humans (2009) Nature medicine 15:380-383.
Watanabe, H., et al. Mechanism of Antiarrhythmic Effects of Flecainide in Catecholaminergic Polymorphic Ventricular Tachycardia(2011) Circ Res 109:712-713.
Wehrens, X. H., et al. Protection from Cardiac Arrhythmia Through Ryanodine Receptor-Stabilizing Protein Calstabin2 (2004) Science 304:292-296.
Xia, C., et al., Regulation of interdomain interactions by calmodulin in inducible nitric-oxide synthase, The J Biol Chem 284:30708-30717, (2009).
Xie, Y., et al., So little source, so much sink: requirements for afterdepolarizations to propagate in tissue, Biophys J 99:1408-1415, (2010).
Xu, X., et al., Defective calmodulin binding to the cardiac ryanodine receptor plays a key role in CPVT-associated channel dysfunction, Biochem Biophys Res Commun 394:660-666, (2010).
Yamaguchi, N., et al., Molecular basis of calmodulin binding to cardiac muscle Ca(2+) release channel (ryanodine receptor), J Biol Chem 278:23480-23486, (2003).
Yang, Y., et al., Cardiac myocyte Z-line calmodulin is mainly RyR2-bound, and reduction is arrhythmogenic and occurs in heart failure, Circ Res 114:295-306, (2014).
Yin, G., et al., Arrhythmogenic calmodulin mutations disrupt intracellular cardiomyocyte Ca2+ regulation by distinct mechanisms, J Am Heart Assoc 3:e000996, (2014).
Yamaguchi et al., Different regions in skeletal and cardiac muscle ryanodine receptors are involved in transducing the functional effects of calmodulin, J Biol Chem., 279:36433-36439, (2004).
Søndergaard et al., Calmodulin mutations causing catecholaminergic polymorphic ventricular tachycardia confer opposing functional and biophysical molecular changes, FEBS J., (2014).
Tikunova et al., Effect of hydrophobic residue substitutions with glutamine on Ca(2+) binding and exchange with the N-domain of troponin C, Biochemistry (Mosc)., 41:6697-6705, (2002).
Ye et al., The complex structure of calmodulin bound to a calcineurin peptide. Proteins., 73:19-27, (2008).
MacQuaide et al., Assessment of sarcoplasmic reticulum Ca2+ depletion during spontaneous Ca2+ waves in isolated permeabilized rabbit ventricular cardiomyocytes, Biophys J., 96:2744-2754, (2009).
Laver, Ca2+ stores regulate ryanodine receptor Ca2+ release channels via luminal and cytosolic Ca2+ sites, Biophys J., 92:3541-3555, (2007).
Györke et al., Regulation of the cardiac ryanodine receptor channel by luminal Ca2+ involves luminal Ca2+ sensing sites, Biophys J., 75:2801-2810, (1998).
Qin et al., Ryanodine receptor luminal Ca2+ regulation: swapping calsequestrin and channel isoforms, Biophys J., 97:1961-1970, (2009).
Chopra et al., Ablation of triadin causes loss of cardiac Ca2+ release units, impaired excitation-contraction coupling, and cardiac arrhythmias, Proc Natl Acad Sci U S A., 106:7636-7641, (2009).
Michael et al., Remodelling of cardiac repolarization: how homeostatic responses can lead to arrhythmogenesis, Cardiovasc Res., 81:491-499, (2009).
Saucerman et al., Calmodulin binding proteins provide domains of local Ca2+ signaling in cardiac myocytes, J Mol Cell Cardiol., 52:312-316, (2012).
Fruen et al., Regulation of the RYR1 and RYR2 Ca2+ release channel isoforms by Ca2+-insensitive mutants of calmodulin, Biochemistry (Mosc)., 42:2740-2747, (2003).
Kalyanasundaram et al., Up-regulation of sarcoplasmic reticulum Ca(2+) uptake leads to cardiac hypertrophy, contractile dysfunction and early mortality in mice deficient in CASQ2. Cardiovasc Res, 98:297-306, (2013).
Makita et al., Novel calmodulin mutations associated with congenital arrhythmia susceptibility, Circ Cardiovasc Genet., 7:466-474, (2014).
Fallon et al., Structure of calmodulin bound to the hydrophobic IQ domain of the cardiac Ca(v)1.2 calcium channel, Struct Lond Engl 1993, 13:1881-1886, (2005).
Garcia et al., Myosin light chain kinase in endothelium: molecular cloning and regulation, Am J Respir Cell Mol Biol., 16:489-494, (1997).
Rellos et al., Structure of the CaMKIIdelta/calmodulin complex reveals the molecular mechanism of CaMKII kinase activation. PLoS Biol., 8:e1000426, (2010).
Vorherr et al., The calmodulin binding domain of nitric oxide synthase and adenylyl cyclase, Biochemistry (Mosc)., 32:6081-6088, (1993).
Viatchenko-Karpinski et al., Abnormal calcium signaling and sudden cardiac death associated with mutation of calsequestrin, Circ Res., 94:471-477, (2004).
Györke et al., Modulation of sarcoplasmic reticulum calcium release by calsequestrin in cardiac myocytes, Biol Res., 37:603-607, (2004).
Terentyev et al., Protein protein interactions between triadin and calsequestrin are involved in modulation of sarcoplasmic reticulum calcium release in cardiac myocytes, J Physiol., 583:71-80, (2007).
Calvert et al., The importance of the carboxyl-terminal domain of cardiac troponin C in Ca2+-sensitive muscle regulation, J Biol Chem., 275:32508-32515, 2000.
Ward et al., Characterization of the interaction between the N-terminal extension of human cardiac troponin I and troponin C, Biochemistry (Mosc), 43:4020-4027, (2004).
Davis et al., Ca(2+) exchange with troponin C and cardiac muscle dynamics, Cardiovasc Res., 77:619-626, (2008).
Xiong et al., Lobe-dependent regulation of ryanodine receptor type 1 by calmodulin, J Biol Chem., 277:40862-40870, (2002).
Davis et al., Mutations of hydrophobic residues in the N-terminal domain of troponin C affect calcium binding and exchange with the troponin C-troponin I96-148 complex and muscle force production, J Biol Chem., 279:17348-17360, (2004).
Norman et al., Modulation of the rate of cardiac muscle contraction by troponin C constructs with various calcium binding affinities, Am J Physiol Heart Circ Physiol, 293:H2580-2587, 2007.

(56) References Cited

OTHER PUBLICATIONS

Wang et al., Noncanonical EF-hand motif strategically delays Ca2+ buffering to enhance cardiac performance, Nat Med., 19:305-312, 2013.

Longyear et al., Ca++-sensitizing mutations in troponin, P(i), and 2-deoxyATP alter the depressive effect of acidosis on regulated thin-filament velocity, J Appl Physiol Bethesda Md 1985, 116:1165-1174, 2014.

Tikunova et al., Designing calcium-sensitizing mutations in the regulatory domain of cardiac roponin C, J Biol Chem., 279:35341-35352, 2004.

Qian et al., Early endosomal escape of a cyclic cell-penetrating peptide allows effective cytosolic cargo delivery, Biochemistry (Mosc)., 53:4034-4046, (2014).

Saha et al., Isolation of primary HIV-1 that target CD8+ T lymphocytes using CD8 as a receptor, Nat Med., 7:65-72, (2001).

Terentyev et al., miR-1 overexpression enhances Ca(2+) release and promotes cardiac arrhythmogenesis by targeting PP2A regulatory subunit B56alpha and causing CaMKII-dependent hyperphosphorylation of RyR2, Circ Res., 104:514-521, (2009).

Radwański et al., Cytosolic calcium accumulation and delayed repolarization associated with ventricular arrhythmias in a guinea pig model of Andersen-Tawil syndrome. Heart Rhythm Off J Heart Rhythm Soc., 7:1428-1435.e1, 2010.

Radwański et al., NCX is an important determinant for premature ventricular activity in a druginduced model of Andersen-Tawil syndrome, Cardiovasc Res., 92:57-66, (2011).

Radwański et al., Inhibition of Na+ channels ameliorates arrhythmias in a druginduced model of Andersen-Tawil syndrome, Heart Rhythm Off J Heart Rhythm Soc., 10:255-263, (2013).

Keurs et al., Calcium and Arrhythmogenesis. Physiol Rev., 87:457-506, (2007).

Kubalova etal., Abnormal intrastore calcium signaling in chronic heart failure. Proc Natl Acad Sci USA, 102:14104-14109, 2005.

International Search Report for PCT/US2016/027889 dated Aug. 19, 2016.

Heo, et al., "Involvement of specific calmodulin isoforms in salicylic acid-independent activation of plant disease resistance responses", Proc. Natl. Acad. Sci. USA, Plant Biology, vol. 96, Jan. 1999, pp. 766-771.

Chin, et al., "Characterization of Substrate Phosphorylation and Use of Calmodulin Mutans to Address Implications from the Enzyme Crystal Structure of Calmodulin-dependent Protein Kinase I*", The Journal of Biological Chemistry, vol. 272, No. 50, Issue of Dec. 12, 1997, pp. 31235-31240.

SEQUENCE LISTING

```
<160> NUMBER OF SEQ ID NOS: 11

<210> SEQ ID NO 1
<211> LENGTH: 149
<212> TYPE: PRT
<213> ORGANISM: Homo sapiens

<400> SEQUENCE: 1

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 2
<211> LENGTH: 149
<212> TYPE: PRT
<213> ORGANISM: Artificial Sequence
<220> FEATURE:
<223> OTHER INFORMATION: Synthetic construct

<400> SEQUENCE: 2

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Gln Arg Ser Leu Gly Gln Asn Pro Thr Glu Ala Glu
        35                  40                  45
```

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
 65                  70                  75                  80

Asp Ser Glu Glu Glu Ile Arg Glu Ala Phe Arg Val Phe Asp Lys Asp
                 85                  90                  95

Gly Asn Gly Tyr Ile Ser Ala Ala Glu Leu Arg His Val Met Thr Asn
                100                 105                 110

Leu Gly Glu Lys Leu Thr Asp Glu Glu Val Asp Glu Met Ile Arg Glu
                115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 3
<211> LENGTH: 149
<212> TYPE: PRT
<213> ORGANISM: Artificial Sequence
<220> FEATURE:
<223> OTHER INFORMATION: Synthetic construct

<400> SEQUENCE: 3

Met Ala Asp Gln Leu Thr Glu Glu Gln Ile Ala Glu Gln Lys Glu Ala
 1               5                  10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
 65                  70                  75                  80

Asp Ser Glu Glu Glu Ile Arg Glu Ala Phe Arg Val Phe Asp Lys Asp
                 85                  90                  95

Gly Asn Gly Tyr Ile Ser Ala Ala Glu Leu Arg His Val Met Thr Asn
                100                 105                 110

Leu Gly Glu Lys Leu Thr Asp Glu Glu Val Asp Glu Met Ile Arg Glu
                115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 4
<211> LENGTH: 149
<212> TYPE: PRT
<213> ORGANISM: Artificial Sequence
<220> FEATURE:
<223> OTHER INFORMATION: Synthetic construct

<400> SEQUENCE: 4

Met Ala Asp Gln Leu Thr Glu Glu Gln Ile Ala Glu Phe Lys Glu Ala
 1               5                  10                  15

Phe Ser Leu Phe Asp Lys Asp Gly Asp Gly Asp Ile Thr Thr Lys Glu
                20                  25                  30

Leu Gly Thr Val Met Arg Ser Leu Gly Gln Asn Pro Thr Glu Ala Glu

```
                35                  40                  45
Leu Gln Asp Met Ile Asn Glu Val Asp Ala Asp Gly Asn Gly Thr Ile
 50                  55                  60

Asp Phe Pro Glu Phe Leu Thr Met Met Ala Arg Lys Met Lys Asp Thr
 65                  70                  75                  80

Asp Ser Glu Glu Glu Ile Arg Glu Ala Phe Arg Val Phe Asp Lys Asp
                 85                  90                  95

Gly Asn Gly Tyr Ile Ser Ala Ala Glu Leu Arg His Val Met Thr Asn
                100                 105                 110

Leu Gly Glu Lys Leu Thr Asp Glu Glu Val Asp Glu Met Ile Arg Glu
            115                 120                 125

Ala Asp Ile Asp Gly Asp Gly Gln Val Asn Tyr Glu Glu Phe Val Gln
        130                 135                 140

Met Met Thr Ala Lys
145

<210> SEQ ID NO 5
<211> LENGTH: 149
<212> TYPE: PRT
<213> ORGANISM: Artificial Sequence
<220> FEATURE:
<223> OTHER INFORMATION: Synthetic construct

<400> SEQUENCE: 5

Met Ala Asp Gln Leu Thr Glu Glu Gln Ile Ala Glu Phe Lys Glu Ala
 1               5                  10                  15

Phe Ser Leu Phe Asp Lys Asp Gly Asp Gly Thr Ile Asp Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
 50                  55                  60

Asp Phe Pro Glu Phe Leu Thr Met Met Ala Arg Lys Met Lys Asp Thr
 65                  70                  75                  80

Asp Ser Glu Glu Glu Ile Arg Glu Ala Phe Arg Val Phe Asp Lys Asp
                 85                  90                  95

Gly Asn Gly Tyr Ile Ser Ala Ala Glu Leu Arg His Val Met Thr Asn
                100                 105                 110

Leu Gly Glu Lys Leu Thr Asp Glu Glu Val Asp Glu Met Ile Arg Glu
            115                 120                 125

Ala Asp Ile Asp Gly Asp Gly Gln Val Asn Tyr Glu Glu Phe Val Gln
        130                 135                 140

Met Met Thr Ala Lys
145

<210> SEQ ID NO 6
<211> LENGTH: 149
<212> TYPE: PRT
<213> ORGANISM: Artificial Sequence
<220> FEATURE:
<223> OTHER INFORMATION: Synthetic construct

<400> SEQUENCE: 6

Met Ala Asp Gln Leu Thr Glu Glu Gln Ile Ala Glu Phe Lys Glu Ala
 1               5                  10                  15

Phe Ser Leu Phe Asp Lys Asp Gly Asp Gly Thr Ile Thr Thr Lys Glu
                20                  25                  30
```

```
Leu Gly Thr Val Met Arg Ser Gln Gly Gln Asn Pro Thr Glu Ala Glu
        35                  40                  45

Leu Gln Asp Met Ile Asn Glu Val Asp Ala Asp Gly Asn Gly Thr Ile
 50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 7
<211> LENGTH: 149
<212> TYPE: PRT
<213> ORGANISM: Artificial Sequence
<220> FEATURE:
<223> OTHER INFORMATION: Synthetic construct

<400> SEQUENCE: 7

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asp Gly Thr Ile
 50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 8
<211> LENGTH: 149
<212> TYPE: PRT
<213> ORGANISM: Artificial Sequence
<220> FEATURE:
<223> OTHER INFORMATION: Synthetic construct

<400> SEQUENCE: 8

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30
```

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
 50                  55                  60

Asp Phe Pro Glu Phe Leu Thr Gln Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
            115                 120                 125

Ala Asp Ile Asp Gly Asp Gly Gln Val Asn Tyr Glu Glu Phe Val Gln
        130                 135                 140

Met Met Thr Ala Lys
145

<210> SEQ ID NO 9
<211> LENGTH: 149
<212> TYPE: PRT
<213> ORGANISM: Artificial Sequence
<220> FEATURE:
<223> OTHER INFORMATION: Synthetic construct

<400> SEQUENCE: 9

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
 50                  55                  60

Asp Phe Pro Glu Phe Leu Thr Met Gln Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
            115                 120                 125

Ala Asp Ile Asp Gly Asp Gly Gln Val Asn Tyr Glu Glu Phe Val Gln
        130                 135                 140

Met Met Thr Ala Lys
145

<210> SEQ ID NO 10
<211> LENGTH: 150
<212> TYPE: PRT
<213> ORGANISM: Glycine max

<400> SEQUENCE: 10

Met Ala Asp Ile Leu Ser Glu Glu Gln Ile Val Asp Phe Lys Glu Ala
1               5                   10                  15

Phe Gly Leu Phe Asp Lys Asp Gly Asp Gly Cys Ile Thr Val Glu Glu
                20                  25                  30

```
Leu Ala Thr Val Ile Arg Ser Leu Asp Gln Asn Pro Thr Glu Glu Glu
        35                  40                  45

Leu Gln Asp Met Ile Ser Glu Val Asp Ala Asp Gly Asn Gly Thr Ile
        50                  55                  60

Glu Phe Asp Glu Phe Leu Ser Leu Met Ala Lys Lys Val Lys Asp Thr
65                      70                  75                  80

Asp Ala Glu Glu Glu Leu Lys Glu Ala Phe Lys Val Phe Asp Lys Asp
                85                  90                  95

Gln Asn Gly Tyr Ile Ser Ala Ser Glu Leu Arg His Val Met Ile Asn
                100                 105                 110

Leu Gly Glu Lys Leu Thr Asp Glu Glu Val Glu Gln Met Ile Lys Glu
            115                 120                 125

Ala Asp Leu Asp Gly Asp Gly Gln Val Asn Tyr Glu Glu Phe Val Lys
            130                 135                 140

Met Met Met Thr Val Arg
145                 150

<210> SEQ ID NO 11
<211> LENGTH: 31
<212> TYPE: PRT
<213> ORGANISM: Homo sapiens

<400> SEQUENCE: 11

Arg Ser Lys Lys Ala Val Trp His Lys Leu Leu Ser Lys Gln Arg Lys
1               5                   10                  15

Arg Ala Val Val Ala Cys Phe Arg Met Ala Pro Leu Tyr Asn Leu
                20                  25                  30
```

ENGINEERED CALMODULIN FOR TREATMENT OF RYANOPATHIES

CROSS-REFERENCE TO RELATED APPLICATIONS

This application is the 35 U.S.C. § 371 national stage application of PCT Application No. PCT/US2016/027889, filed Apr. 15, 2016, which claims benefit of U.S. Provisional Application No. 62/147,903, filed Apr. 15, 2015, both of which are herein incorporated by reference in their entireties.

STATEMENT REGARDING FEDERALLY SPONSORED RESEARCH OR DEVELOPMENT

This invention was made with Government Support under Grant No. HL091986 awarded by the National Institutes of Health. The Government has certain rights in the invention.

BACKGROUND

The generation of the heartbeat relies on Ca-dependent Ca release (CICR) from the sarcoplasmic reticulum (SR) via the cardiac ryanodine receptor (RyR2) channels (Bers, D. M. (2002) Nature 415:198-205). As a classical auto-catalytic signal amplification process, CICR requires robust containment mechanism(s) for the maintenance of its stability (Radwanski, P. B., et al. (2013) J Mol Cell Cardiol 58:77-83). Indeed, dysregulated RyR2-mediated Ca release manifests in spontaneous Ca oscillations resulting in life-threatening cardiac arrhythmias and cardiomyopathy (Radwanski, P. B., et al. (2013) J Mol Cell Cardiol 58:77-83; Belevych, A. E., et al. (2012) Circ Res 110:569-577; Belevych, A. E., et al. (2013) Cardiovascular research 98:240-247). These Ca-dependent cardiac diseases and disorders ("ryanopathies") are among the leading causes of hospitalization and death in the US. The link between RyR2 dysfunction and arrhythmia is especially evident in catecholaminergic polymorphic ventricular tachycardia (CPVT), an arrhythmia syndrome caused by mutations in RyR2 or other proteins of the RyR2 complex, including CASQ2 and CaM (Venetucci, L., et al. (2012) Nat Rev Cardiol 9:561-575). CPVT arrhythmogenesis involves aberrant spontaneous Ca release via dysregulated RyR2s (Venetucci, L., et al. (2012) Nat Rev Cardiol 9:561-575; Gyorke, S., et al. (2008) Cardiovascular research 77:245-255). This Ca elevation in turn activates Ca-dependent depolarizing currents that cause DADs and arrhythmic ectopic activity. A similar mechanism appears to account for acquired ryanopathies (i.e., atrial fibrillation, dilated/ischemic/idiopathic heart failure, ventricular arrhythmias, cardiac hypertrophy, impaired exercise capacity, sinoatrial node dysfunction, etc.) associated with abnormal posttranslational modification of RyR2 through phosphorylation and oxidation (Belevych, A. E., et al. (2013) Cardiovasc Res 98:240-247). Because of its central role in pathologic Ca signaling, RyR2 is a logical target for cardiac therapy. Indeed, pharmacological inhibition/stabilization of RyR2 (Jung, C. B., et al. (2012) EMBO Mol Med 4:180-191; Kobayashi, S., et al. (2010) Circ J 74:2579-2584; Watanabe, H., et al. (2011) Circ Res 109:712-713; Lehnart, S. E., et al. (2006) Proc Natl Acad Sci USA 103:7906-7910) (with dantrolene, flecainide and JTV519) has been reported to improve myocyte Ca handling and alleviate arrhythmia burden in preclinical and small clinical studies (Brunello, L., et al. (2013) Proc Natl Acad Sci USA 110:10312-10317; Watanabe, H., et al. (2009) Nature medicine 15:380-383; Wehrens, X. H., et al. (2004) Science 304:292-296; van der Werf, C., et al. (2011) J Am Coll Cardiol 57:2244-2254).

Despite these promising therapeutic modalities, effective and safe RyR2-based anti-arrhythmia therapies for broad application irrespective of ryanopathic etiology are lagging. This lack of progress can be attributed to several issues, most importantly: 1) lack of cardiac specificity of the promising reagents (dantrolene); 2) pro-arrhythmic adverse effects (flecainide); and 3) insufficient understanding of RyR2 regulation and Ca handling impeding the development of new therapies.

Additionally, ryanopathies in the brain and skeletal muscle due to leaky RyR has been associated with duschenne muscular dystrophy, malignant hyperthermia, seizures, cognitive disorders, diabetes, and heat stroke (Santulli G, Marks A R (2015) Current Mol Pharmac 8:206-222; Liu X et al., (2012) Cell 150:1055-1067).

SUMMARY

Compositions and methods are disclosed for altering the binding affinity of calmodulin for ryanodine receptor 2 (RyR2). As disclosed herein, these therapeutic calmodulin (TCaM) proteins can be used to correct ryanopathies in heart, brain, and skeletal muscle by, for example, prolonging the RyR refractory period.

For example, TCaM proteins are disclosed that have an affinity for human RyR2 that is at least 2, 3, 4, 5, 6, 7, 8, 9, 10 fold higher than wildtype human calmodulin (hCaM). For example, the TCaM protein can have a Kd value that is that is at least 2, 3, 4, 5, 6, 7, 8, 9, 10 fold lower than hCaM. In some embodiments, human CaM binds RyR2 with a Kd of about 0.5 µM. In some embodiments, the TCaM protein can have a Kd value that is that is less than 0.2 µM, 0.1 µM, 90 nM, 80 nM, 70 nM, 60 nM, or 50 nM.

In some embodiments, the disclosed TCaM has an N-terminal calcium dissociation rate that is at least 2, 3, 4, 5, 6, 7, 8, 9, 10 fold slower than hCaM. In some embodiments, hCaM has an N-terminal calcium dissociation rate of 1000/sec. In some embodiments, the TCaM has an N-terminal calcium dissociation rate 500/sec, 400/sec, 300/sec, 200/sec, or 100/sec.

In some embodiments, the TCaM protein is a mutant form of a wildtype CaM. Amino acid residues in CaM responsible for RyR2 affinity are disclosed; these residues can therefore be mutated to modify the binding affinity.

For example, an isolated polypeptide is disclosed having the amino acid sequence of wildtype human CaM (e.g., SEQ ID NO: 1) with at least one mutation selected from the group consisting of F13Q, T27D, T29D, M37Q, L40Q, N61D, M72Q, and M73Q. The preferred affinity can be selected based on the selection of mutation and/or mutation combination. In some embodiments, the polypeptide has 1, 2, 3, 4, 5, 6, or 7 of these mutations.

In particular embodiments, the polypeptide has a M37Q mutation. Therefore, disclosed is a polypeptide having the amino acid sequence SEQ ID NO:2.

In some embodiments, the TCaM comprises a plant calmodulin having a higher or lower affinity for human RyR2 than hCaM. For example, the TCaM can comprises a soybean calmodulin, such as the one set forth in amino acid sequence SEQ ID NO: 10.

In some embodiments, the disclosed polypeptide is cyclic. Cyclic peptides are polypeptide chains wherein the amino termini and carboxyl termini, amino termini and side chain, carboxyl termini and side chain, or side chain and side chain are linked with a covalent bond that generates the ring.

In some embodiments, the polypeptide is further modified to promote stability, affinity, and/or bioavailability. For example, in some embodiments, the polypeptide contains an N-terminal glutathione (GSH). Glutathione (GSH) is an important antioxidant in plants, animals, fungi, and some bacteria and archaea, preventing damage to important cellular components caused by reactive oxygen species such as free radicals, peroxides, lipid peroxides and heavy metals. It is a tripeptide with a gamma peptide linkage between the carboxyl group of the glutamate side-chain and the amine group of cysteine (which is attached by normal peptide linkage to a glycine).

Also disclosed are isolated polynucleotides comprising a nucleic acid sequence encoding a TCaM polypeptide disclosed herein. In some embodiments, the nucleic acid sequence encoding the TCaM polypeptide is operably linked to an expression control sequence. These polynucleotides can be contained in expression vectors and/or delivery vectors. In some embodiments, the vector is a viral vector suitable for cardiac gene delivery. For example, in some cases, the viral vector is an adenoassociated virus (AAV).

Also disclosed is a method for treating a ryanopathy-associated disease in a subject that involves administering to the subject a composition comprising a TCaM disclosed herein. In some embodiments, the ryanopathy-associated disease comprises a catecholaminergic polymorphic ventricular tachycardia (CPVT). In some embodiments, the ryanopathy-associated disease is selected from the group consisting of dilated, ischemic or idiopathic heart failure; atrial fibrillation; cardiac hypertrophy; impaired exercise capacity; sinoatrial node dysfunction; and ventricular arrhythmia. In some embodiments, the ryanopathy-associated disease is selected from the group consisting of duchenne muscular dystrophy, malignant hyperthermia, seizures, cognitive disorders, diabetes, and heat stroke.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows CPVT CaM N98S increases Ca waves (f wave) frequency and shortens Ca release refractoriness in permeabilized WT murine myocytes. Refractoriness factor (RF) was calculated as inverse to spark frequency (f spark) occurring within one second following Ca wave. FIG. 3B shows patched canine myocytes stimulated at 0.5 Hz using a 'typical' control action potential (AP-clamp) waveform in the presence of 100 nM isoproterenol, a beta-adrenergic agonist. FIG. 3C shows CPVT CaM accelerated the N-terminal rates of Ca dissociation from CaM-RyR2 complex (left).

FIG. 4A shows CaM-D57A accelerates Ca dissociation rate from N(left)- but not from the C(right)-terminus of CaM-RyR2. FIG. 4B shows CaM-D57A increases frequency of Ca waves and Ca sparks, and reduced RF in permeabilized WT murine myocytes.

FIG. 7A shows TCaM reduces f wave in intact myocytes isolated from R33Q mice. FIG. 7B shows representative surface ECG traces from R33Q mice treated with wt CaM and TCaM.

FIG. 8A shows CaM conjugation with cyclic peptides. FIG. 8B shows delivery efficacy in intact WT murine myocytes.

FIG. 9A shows Ca dissociation rate from CaM is target-dependent. FIG. 9B shows Ca dissociation rate from CaM N-terminal in the presence of RyR2 (left) or Cav1.2 (right).

FIG. 11A shows bright field illuminated isolated cardiac myocytes from mouse that was injected via the thoracic cavity with AAV9. FIG. 11B shows mCherry fluorescence of the myocytes shown in FIG. 11A. FIG. 11C shows mCherry fluorescence in RH-237-stained (cell membrane) trabeculae. FIG. 11D shows GFP fluorescence from LV tissue harvested from a WT mouse injected at 2 days of age with IP delivered AAV9 GFP.

FIG. 13A is a 2D mage of RH237-stained Purkinje fibers (PF) preparation. FIG. 13B contains line-scans from the Purkinje fiber in FIG. 13A depicting changes in intracellular Ca (top) and membrane potential (bottom).

FIG. 14A shows effects of wt and N54I CaMs assessed in permeabilzed canine myocytes using cytosolic (Rhod-2) and SR-loaded (Fluo-5N) Ca dyes. FIG. 14B shows N54I CaM speeds up recovery of Ca sparks following Ca wave-mediated SR Ca depletion.

DETAILED DESCRIPTION

Definitions

Figure 1:
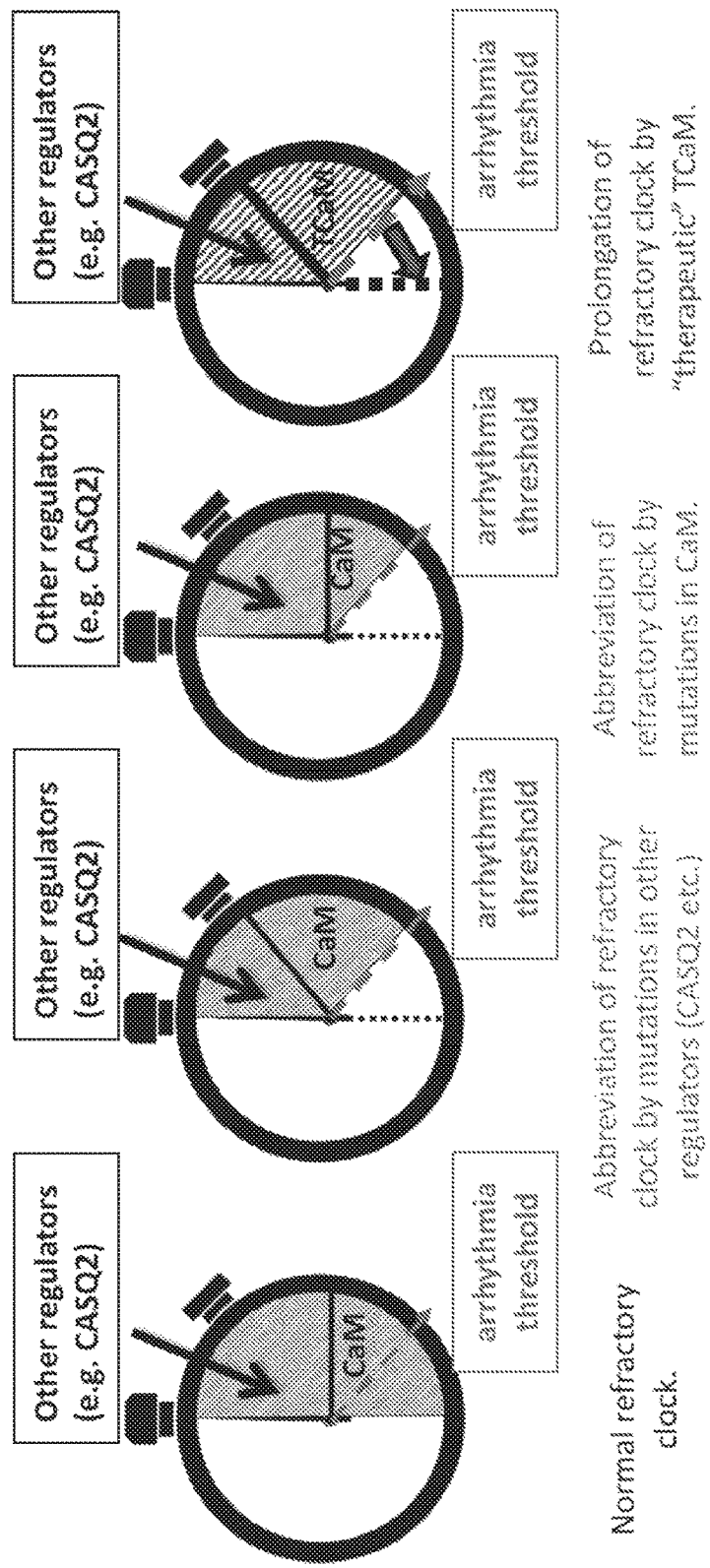
FIG. 1 illustrates RyR2's "Refractory clock" and Arrhythmia. The refractory period for RyR2 is regulated by a number of factors including CASQ2 and CaM. If the refractory period is shortened past a threshold, arrhythmia can occur. However, the refractoriness can be prolonged by application of a "therapeutic" CaM (TCaM).

As used herein, the term "ryanopathy" refers to the inability of a ryanodine receptor (RyR) to appropriately deactivate and become/remain refractory. In cardiomyocytes, this can result in calcium release-related contractile dysfunction and spontaneous activity.

The term "ryanopathy-associated disease" refers to any disease, disorder, or medical condition caused or exacerbated by ryanopathy.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "peptide," "protein," and "polypeptide" are used interchangeably to refer to a natural or synthetic molecule comprising two or more amino acids linked by the carboxyl group of one amino acid to the alpha amino group of another. The term "polypeptide" encompasses naturally occurring or synthetic molecules.

The term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "transformation" and "transfection" mean the introduction of a nucleic acid, e.g., an expression vector, into a recipient cell including introduction of a nucleic acid to the chromosomal DNA of said cell.

Therapeutic Calmodulin (TCaM)

Compositions and methods are disclosed for altering the binding affinity of calmodulin for ryanodine receptor 2 (RyR2). As disclosed herein, these therapeutic calmodulin (TCaM) proteins can be used to correct ryanopathies by, for example, prolonging the RyR2 refractory period.

For example, TCaM proteins are disclosed that have an affinity for human RyR2 that is at least 2, 3, 4, 5, 6, 7, 8, 9, 10 fold higher than wildtype human calmodulin (hCaM). For example, the TCaM protein can have a Kd value that is that is at least 2, 3, 4, 5, 6, 7, 8, 9, 10 fold lower than hCaM. In some embodiments, human CaM binds RyR2 with a Kd of about 0.5 μM. In some embodiments, the TCaM protein can have a Kd value that is that is less than 0.2 μM, 0.1 μM, 90 nM, 80 nM, 70 nM, 60 nM, or 50 nM. Such binding affinities can be measured by any method known in the art, such as radioimmunoassay, ELISA, surface plasmon resonance (SPR) based technology (e.g., Biacore) analysis, or kinetic exclusion assay (e.g., KinExA). The affinity data may be analyzed, for example, by the method of Scatchard et al., Ann N.Y. Acad. Sci., 51:660 (1949).

In some embodiments, the disclosed TCaM has an N-terminal calcium dissociation rate that is at least 2, 3, 4, 5, 6, 7, 8, 9, 10 fold slower than hCaM. In some embodiments, hCaM has an N-terminal calcium dissociation rate of 1000/sec. In some embodiments, the TCaM has an N-terminal calcium dissociation rate 500/sec, 400/sec, 300/sec, 200/sec, or 100/sec. Calcium dissociation can be measured, for example, with a stopped-flow instrument. A stopped-flow instrument is a rapid mixing device used to study the chemical kinetics of fast reactions in solution. In stopped-flow technique, the solutions are forced from syringes into a mixing chamber. After a very short period of flow, perhaps a few ms, the flow is stopped suddenly when the observation cell is filled by an opposing piston that is linked to a sensing switch that triggers the measuring device. Small volumes of solutions are used, and the kinetic equations for modeling the reactions are equivalent to those used in conventional methods in which concentration and time are measured. Stopped-flow is useful for studying fast reactions that have half-lives as short as a few milliseconds.

In some embodiments, the TCaM protein is a mutant form of a wildtype CaM. Amino acid residues in CaM responsible for RyR2 affinity are disclosed; these residues can therefore be mutated to modify the binding affinity.

For example, an isolated polypeptide is disclosed having the amino acid sequence of wildtype human CaM with at least one mutation at amino acid positions F13, T27, T29, M37, L40, N61, M72, or M73. For example, the polypeptide can have at least one mutation selected from the group consisting of F113Q, T27D, T29D, M37Q, L40Q, N61D, M72Q, and M73Q. The preferred affinity can be selected based on the selection of mutation and/or mutation combination. In some embodiments, the polypeptide has 1, 2, 3, 4, 5, 6, or 7 of these mutations.

The following is an amino acid sequence for human CaM: MADQLTEEQI AEFKEAFSLF DKDGDGT<u>T</u>T KELGTV M<u>RSL</u> GQNPTEAELQ DMINEVDADG <u>N</u>GTIDFPEFL T MM ARKMKDT DSEEEIREAF RVFDKDGNGY ISAAELRHVM TNLGEKLTDE EVDEMIREAD IDGDGQVNYE EFVQMMTAK (SEQ ID NO: 1). In some embodiments, the underlined amino acids can be mutated to alter the affinity of CaM for RyR2. Therefore, in some embodiments, the polypeptide has the amino acid sequence SEQ ID NO: 1 with at least one mutation at amino acid positions F13, T27, T29, M37, L40, N61, M72, or M73.

In some embodiments, the polypeptide has a M37Q mutation. Therefore, disclosed is a polypeptide having the amino acid sequence MADQLTEEQI AEFKEAFSLF DKDGDGTITT KELGTV<u>Q</u>RSL GQNPTEAELQ DMINEVDADG NGTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:2).

In some embodiments, the polypeptide has an F13Q mutation. Therefore, also disclosed is a polypeptide having the amino acid sequence MADQLTEEQI AE<u>Q</u>KEAFSLF DKDGDGTITT KELGTVMRSL GQNPTEAELQ DMINEVDADG NGTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:3).

In some embodiments, the polypeptide has a T27D mutation. Therefore, also disclosed is a polypeptide having the amino acid sequence MADQLTEEQI AEFKEAFSLF DKDGDG<u>D</u>ITT KELGTVMRSL GQNPTEAELQ DMINEVDADG NGTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:4).

In some embodiments, the polypeptide has a T29D mutation. Therefore, also disclosed is a polypeptide having the amino acid sequence MADQLTEEQI AEFKEAFSLF DKDGDGTI<u>D</u>T KELGTVMRSL GQNPTEAELQ DMINEVDADG NGTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:5).

In some embodiments, the polypeptide has an L40Q mutation. Therefore, also disclosed is a polypeptide having the amino acid sequence MADQLTEEQI AEFKEAFSLF DKDGDGTITT KELGTVMRS<u>Q</u> GQNPTEAELQ DMINEVDADG NGTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:6).

In some embodiments, the polypeptide has an N61D mutation. Therefore, also disclosed is a polypeptide having the amino acid sequence MADQLTEEQI AEFKEAFSLF DKDGDGTITT KELGTVMRSL GQNPTEAELQ DMINEVDADG <u>D</u>GTIDFPEFL TMMARKMKDT DSEEEIREAF RVFDKDGNGY ISAAELRHVM TNLGEKLTDE EVDEMIREAD IDGDGQVNYE EFVQMMTAK (SEQ ID NO:7).

In some embodiments, the polypeptide has an M72Q mutation. Therefore, also disclosed is a polypeptide having the amino acid sequence MADQLTEEQI AEFKEAFSLF DKDGDGTITT KELGTVMRSL GQNPTEAELQ DMINEVDADG NGTIDFPEFL T<u>Q</u>MARKMKDT DSEEEIREAF RVFDKDGNGY ISAAELRHVM TNLGEKLTDE EVDEMIREAD IDGDGQVNYE EFVQMMTAK (SEQ ID NO:8).

In some embodiments, the polypeptide has an M73Q mutation. Therefore, also disclosed is a polypeptide having the amino acid sequence MADQLTEEQI AEFKEAFSLF DKDGDGTITT KELGTVMRSL GQNPTEAELQ DMINEVDADG NGTIDFPEFL TM<u>Q</u>ARKMKDT DSEEEIREAF RVFDKDGNGY ISAAELRHVM TNLGEKLTDE EVDEMIREAD IDGDGQVNYE EFVQMMTAK (SEQ ID NO:9).

In some embodiments, the TCaM comprises a plant calmodulin having a higher or lower affinity for human RyR2 than hCaM. For example, the TCaM can comprises a soybean calmodulin, such as Soybean Calmodulin 4. In some embodiments, the polypeptide has the amino acid sequence MADILSEEQI VDFKEAFGLF DKDGDGCITV EELATVIRSL DQNPTEEELQ DMISEVDADG NGTIEFDEFL SLMAKKVKDT DAEEELKEAF KVFDKDQNGY ISASELRHVM INLGEKLTDE EVEQMIKEAD LDGDGQVNYE EFVKMMMTVR (SEQ ID NO:10).

In some embodiments, the disclosed polypeptide is cyclic. Cyclic peptides are polypeptide chains wherein the amino termini and carboxyl termini, amino termini and side chain, carboxyl termini and side chain, or side chain and side chain are linked with a covalent bond that generates the ring.

Cyclic peptides can be classified according to the types of bonds that comprise the ring. Homodetic cyclic peptides, such as cyclosporine A, are those in which the ring is composed exclusively of normal peptide bonds (i.e. between the alpha carboxyl of one residue to the alpha amine of another). Cyclic isopeptides contain at least one non-alpha amide linkage, such as a linkage between the side chain of one residue to the alpha carboxyl group of another residue, as in microcystin and bacitracin. Cyclic depsipeptides have at least one lactone (ester) linkage in place of one of the amides. Some cyclic depsipeptides are cyclized between the C-terminal carboxyl and the side chain of a Thr or Ser residue in the chain. Bicyclic peptides contain a bridging group, generally between two of the side chains.

Cyclic peptides tend to be extremely resistant to the process of digestion, enabling them to survive in the human digestive tract. This trait makes cyclic peptides attractive to designers of protein-based drugs that may be used as scaffolds which, in theory, could be engineered to incorporate any arbitrary protein domain of medicinal value, in order to allow those components to be delivered orally. Cyclic peptides are also "rigid" compared to the corresponding linear peptides, and this attribute promotes binding by removing the "entropic penalty".

In some embodiments, the polypeptide is further modified to promote stability, affinity, and/or bioavailability. For example, in some embodiments, the polypeptide contains an N-terminal glutathione (GSH). Glutathione (GSH) is an important antioxidant in plants, animals, fungi, and some bacteria and archaea, preventing damage to important cellular components caused by reactive oxygen species such as free radicals, peroxides, lipid peroxides and heavy metals. It is a tripeptide with a gamma peptide linkage between the carboxyl group of the glutamate side-chain and the amine group of cysteine (which is attached by normal peptide linkage to a glycine).

Pharmaceutical Compositions

Disclosed is a pharmaceutical compositions containing therapeutically effective amounts of one or more of the disclosed TCaMs and a pharmaceutically acceptable carrier. Pharmaceutical carriers suitable for administration of the compounds provided herein include any such carriers known to those skilled in the art to be suitable for the particular mode of administration.

In addition, the TCaMs may be formulated as the sole pharmaceutically active ingredient in the composition or may be combined with other active ingredients. For example, the TCaMs may be formulated or combined with known NSAIDs, anti-inflammatory compounds, steroids, and/or antibiotics.

The TCaMs are, in some embodiments, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In some embodiments, the TCaMs described above are formulated into pharmaceutical compositions using techniques and procedures well known in the art.

In some embodiments, the TCaMs are formulated for single dosage administration. The TCaMs is included in the pharmaceutically acceptable carrier in an amount sufficient to exert a therapeutically useful effect in the absence of undesirable side effects on the patient treated. The therapeutically effective concentration may be determined empirically by testing the TCaMs in in vitro, ex vivo and in vivo systems, and then extrapolated therefrom for dosages for humans.

In instances in which the TCaMs exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Liquid pharmaceutically administrable compositions can, for example, be prepared by dissolving, dispersing, or otherwise mixing a TCaMs as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Methods of Treating Ryanopathy-Associated Diseases

The cardiac ryanodine receptor (RyR2), a $Ca^{2+}$ release channel on the membrane of the sarcoplasmic reticulum (SR), plays a key role in determining the strength of the heartbeat by supplying $Ca^{2+}$ required for contractile activation. Abnormal RyR2 function is recognized as an important part of the pathophysiology of heart failure (HF) and arrhythmias. While in the normal heart, the balance between the cytosolic and intra-SR $Ca^{2+}$ regulation of RyR2 function maintains the contraction-relaxation cycle, in HF, this behavior is compromised by excessive post-translational modifications of the RyR2. Such modification of the $Ca^{2+}$ release channel impairs the ability of the RyR2 to properly deactivate leading to a spectrum of $Ca^{2+}$-dependent pathologies that include cardiac systolic and diastolic dysfunction, arrhythmias, and structural remodeling. This set of conditions associated with RyR2 dysfunction have been dubbed as 'ryanopathy'.

As disclosed herein, therapeutic calmodulin (TCaM) proteins can correct ryanopathies by, for example, prolonging the RyR2 refractory period.

Therefore, also disclosed is a method for treating a ryanopathy-associated disease in a subject that involves administering to the subject a composition comprising a TCaM protein disclosed herein.

Also disclosed is a method for treating a ryanopathy-associated disease in a subject that involves administering to the subject a composition comprising a vector containing a nucleic acid encoding a TCaM disclosed herein.

Preferred vectors include viral vectors, lipid-based vectors and other vectors that are capable of delivering DNA to non-dividing cells in vivo. Presently preferred are viral vectors, particularly replication-defective viral vectors.

In some embodiments, the viral vector is an adenovirus (Ad) or adeno-associated virus (AAV). Both human and non-human viral vectors can be used but preferably the recombinant viral vector is replication-defective in humans. Where the vector is an adenovirus, it preferably comprises a polynucleotide having a promoter operably linked to a gene encoding the TCaM, and is replication-defective in humans. Presently preferred replication-defective adenoviral vector have deletions that remove the E1A and E1B genes, or have deletions that remove the E1A, E1B and E4 genes.

AAV vectors provide for sustained, long-term gene expression in a wide variety of tissues and cause minimal immunological complications compared to other viral vectors being tested for gene therapy. In recent years, a variety of new AAV serotypes have been isolated that exhibit a wide range of tissue tropisms and provide for efficient transduction and long-term gene expression. In particular, serotypes AAV6, AAV8, and AAV9 transduce cardiomyocytes preferentially following systemic administration and provide uniform gene delivery throughout the myocardium. The most widely studied serotype, AAV2, has a prolonged lag phase of 4-6 weeks before reaching maximum gene expression in the heart. On the other hand, the more recently discovered AAV serotypes provide for an earlier onset of gene expression, approaching steady state levels within 2-3 weeks.

AAV vectors preferably comprise a polynucleotide having a promoter operably linked to a gene encoding the TCaM and, preferably, the gene encoding the TCaM is flanked by AAV inverted terminal repeats (ITRs). Preferably, the AAV vector is replication-defective in humans. Presently preferred replication-defective AAV vectors have deletions affecting one or more AAV replication or encapsidation sequences. Alternatively, the vector can be a lipid-based vector comprising a gene encoding the TCaM as described herein.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant. In some embodiments, the pharmaceutical composition is administered to the heart, e.g., by intracoronary injection.

In one embodiment, the pharmaceutical composition is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of the pharmaceutical composition administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Viral vectors can be administered by injection into a blood vessel directly supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium. By injecting the vector stock deeply into the lumen of one or both coronary arteries (or grafts and other vascular conduits), preferably into both the right and left coronary arteries (or grafts and other vascular conduits), and preferably in an amount of $10^7$-$10^{13}$ viral particles as determined by optical densitometry (more preferably $10^9$-$10^{11}$ viral particles), it is possible to locally transfect a desired number of cells, especially cardiac myocytes, with genes that encode TCaMs into the myocardium, thereby maximizing therapeutic efficacy of gene transfer, and minimizing undesirable effects at extracardiac sites and the possibility of an inflammatory response to viral proteins.

In some embodiments, the ryanopathy-associated disease of the disclosed methods comprises a catecholaminergic polymorphic ventricular tachycardia (CPVT). In some embodiments, the ryanopathy-associated disease is selected from the group consisting of dilated, ischemic or idiopathic heart failure; atrial fibrillation; cardiac hypertrophy; impaired exercise capacity; sinoatrial node dysfunction; and ventricular arrhythmia. In some embodiments, the ryanopathy-associated disease is selected from the group consisting of duchenne muscular dystrophy, malignant hyperthermia, seizures, cognitive disorders, diabetes, and heat stroke Gene Editing Also disclosed is a method for treating a ryanopathy-associated disease in a subject that involves editing the CaM genes of the subject to contain at least one mutation at amino acid positions F13, T27, T29, M37, L40, N61, M72, or M73. For example, the CaM genes can be edited to have at least one mutation selected from the group consisting of F13Q, T27D, T29D, M37Q, L40Q, N61D, M72Q, and M73Q.

The recently described method based on the bacterial clustered regularly interspaced short palindromic repeats (CRISPR) system is a promising tool for gene editing in mammals and offers a unique opportunity to irreversibly modify a gene and develop therapeutic strategies based on DNA editing/repair. The CRISPR system contains two components: (i) a dual crRNA:tracrRNA which was engineered as an artificial single guide RNA (sgRNA) of approximately 20 nucleotides recognizing the target sequence by Watson-Crick base-pairing fused with the tracrRNA at the 3' side of the guide sequence that bind to Cas9 (tracrRNA), (ii) the second component of the system is the CRISPR-associated protein Cas9 nuclease cleaving at the target site. Any sequence of approximately 23 nucleotides including the protospacer adjacent motif at the 3' end of the target sequence (PAM=NGG or NAG for Cas9) and located on both strands of DNA could be a CRISPR target sequence, which provides a large number of potential targets for each gene and greatly facilitates the development of DNA repair strategies compared to the other systems. The DNA endonuclease binds targeted nucleotides to perform double-strand breaks (DSB) and non-homologous end joining (NHEJ) with insertions or deletions (indels) in the sequence created by the cellular repair machinery. When an exogenous DNA sequence with homology with the target sequence is added, HR and integration into the desired locus is occurring after the DSB.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Despite extensive efforts, the robust and specific means of CICR control and specifically how RyR2s become pathologically altered to lead to arrhythmia remain to be elucidated. Yet, clear understanding of these control mechanisms is essential for the design of effective antiarrhythmic therapies. Two alternative control mechanisms have been discussed in the literature to account for the stability of CICR in cardiac cells. Early observations suggested that the elevation of cytosolic [Ca] inhibits further RyR2 Ca release, i.e. Ca-dependent inactivation, by acting on Ca-inactivation sites on RyR2 or an associated protein (Fabiato, A. (1985) J Gen Physiol 85:247-289). More recent evidence has suggested the Ca binding protein CaM contributes to Ca-dependent inactivation (Balshaw, D. M., et al. (2001) J Biol Chem 276:20144-20153; Yamaguchi, N., et al. (2003) J Biol Chem 278:23480-23486; Guo, T., et al. (2011) Biophysical journal 101:2170-2177; Yang, Y., et al. (2014) Circ Res 114:295-306). Alternatively, the decline in luminal Ca following SR Ca release results in deactivation of RyR2 (i.e., store-dependent deactivation), rendering them refractory during the succeeding diastolic period (Radwanski, P. B., et al. (2013) J Mol Cell Cardiol 58:77-83; Brunello, L., et al. (2013) Proc Natl Acad Sci USA 110:10312-10317; Stevens, S. C., et al. (2009) J Physiol 587:4863-4872). Store-dependent deactivation has been suggested to be controlled by CASQ2, which interacts with RyR2 through the integral SR membrane protein triadin (TRD) (Qin, J., et al. (2008) J Gen Physiol 131:325-334; Gyorke, I., et al. (2004) Biophys J 86:2121-2128; Beard, N. A., et al. (2005) Biophys J 88:3444-3454; Terentyev, D., et al. (2003) Proc Natl Acad Sci USA 100:11759-11764). Thus, the functional quiescence, or refractoriness of RyR2s, during the diastolic period has been attributed to the inhibitory influence of either elevated cytosolic Ca or lowered luminal Ca following systolic Ca release.

In this example, rather than viewing cytosolic Ca-dependent inactivation and store-dependent deactivation as competing and alternative possibilities, it is proposed that these mechanisms act in parallel by jointly contributing to the overall refractoriness of RyR2. In support of the roles of both proteins in the control of SR Ca release, separate mutations in both CaM and CASQ2 have been shown to lead to CPVT through dysregulation of RyR2 and aberrant Ca release (Brunello, L., et al. (2013) Proc Natl Acad Sci USA 110:10312-10317; Hwang, H. S., et al. (2014) Circ Res 114:1114-1124). In addition to these molecular mechanisms, other factors appear to influence RyR2 refractoriness and arrhythmia vulnerability, including altered RyR2 phosphorylation and oxidation (Belevych, A. E., et al. (2012) Circ Res 110:569-577) Therefore, different regulatory influences (e.g. cytosolic and luminal Ca, RyR phosphorylation and oxidation statuses, etc), may converge to influence RyR2 refractoriness thereby forming a composite Ca signaling refractoriness clock. An important implication of this concept is that rather than correcting each individual specific molecular defect, ryanopathies of various molecular etiologies can be targeted by a common RyR2-stabilizing factor such as, therapeutic CaMs (TCaMs) that act by resetting the composite refractoriness clock (FIG. 1).

A key question regarding the genesis of arrhythmia is how spontaneous/aberrant Ca release in individual cells leads to triggered activity in the myocardium made of electrically-coupled myocytes. Indeed the depolarizing currents generated in individual cells are expected to dissipate into the neighboring electrically coupled cells (i.e. "current sink-source mismatch"), thus dampening DADs. Recent evidence have demonstrated that in settings of CPVT spontaneous release occurs simultaneously in many cells thereby giving rise to DADs sufficiently high to elicit self-regenerating APs, the basis for ectopic beats (Brunello, L., et al. (2013) Proc Natl Acad Sci USA 110:10312-10317; Kornyeyev, D., et al. (2012) J Mol Cell Cardiol 52:21-31). Abbreviation of RyR2 refractoriness coupled with the capacity of the tissue-wide systolic Ca release to align the composite refractoriness clocks of individual cells provides a dynamic substrate for spatiotemporal synchronization of aberrant diastolic release in the paced myocardium. Moreover, slowing refractoriness (prolonging the timing of the clock) towards its physiological length via pharmacological stabilization of RyR2s results in preventing uniform aberrant release and alleviates ectopic activity in the CPVT myocardium (Brunello, L., et al. (2013) Proc Natl Acad Sci USA 110:10312-10317). In this example, experiments were conducted to determine whether therapeutic targeting of RyR2 refractoriness by therapeutic CaMs to desynchronize aberrant diastolic release alleviate Ca dependent arrhythmia.

Figure 2:
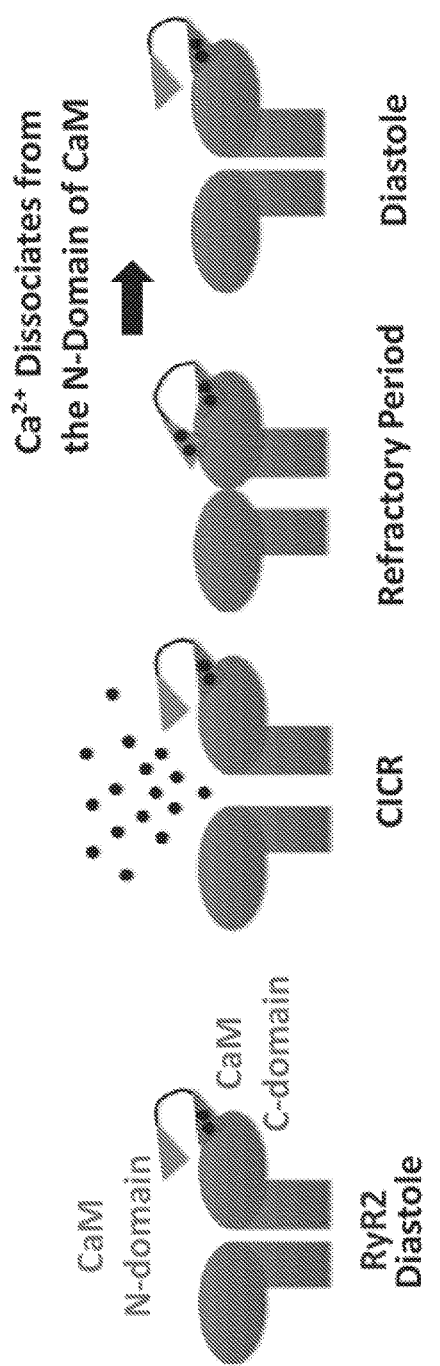
FIG. 2 is a schematic model for CaM Regulation of RyR2.

CaM is a versatile Ca-sensitive modulator of numerous enzymes, ion channels and contractile machinery in the heart, including RyR2, Cav1.2 and CaMKII (Sorensen, A. B., et al. (2013) The FEBS journal 280:5511-5532). Structurally, CaM is composed of two globular domains connected by a central helix (Sorensen, A. B., et al. (2013) The FEBS journal 280:5511-5532). Each domain contains two cooperative EF-hand Ca binding sites that work together to transition the domain from a closed to an open state to render Ca-dependent regulation of effector function. CaM binds to RyR2 at resting Ca through the high Ca affinity C-domain. Upon elevation of cytosolic Ca, CaM inhibits RyR2 activity through binding of the low Ca affinity N-domain (FIG. 2). Recently several mutations in CaM (e.g. N54I and N98S) have been linked to CPVT similar to those caused by mutations in RyR2 and CASQ2 (Hwang, H. S., et al. (2014) Circ Res 114:1114-1124; Nyegaard, M., et al. (2012) American journal of human genetics 91:703-712; Sondergaard, M. T., et al. (2015) The FEBS journal 282:803-816). Interestingly, other CaM mutations have been reported to result in long-QT arrhythmia (Hwang, H. S., et al. (2014) Circ Res 114:1114-1124; Limpitikul, W. B., et al. (2014) J Mol Cell Cardiol 74:115-124). Moreover these different mutations have been reported to selectively affect CaM regulation of two different targets, namely RyR2 and Cav1.2, respectively (Hwang, H. S., et al. (2014) Circ Res 114:1114-1124; Limpitikul, W. B., et al. (2014) J Mol Cell Cardiol 74:115-124). Given CaM's promiscuity it was unclear how different CaM mutations can selectively affect CaM's interactions with different targets to cause different forms of Ca-dependent arrhythmia, which is intriguing and had no explanation. Considering the crystal structure of CaM and based on preliminary results, it was proposed that binding of CaM to structurally distinct interaction sites selectively affects CaM's Ca-binding/unbinding properties through a retrograde allosteric action on CaM. Such a "molding by target" mechanism where the lock modifies the key could convey unique specificity to CaM/Ca signaling with respect to different targets and account for the capacity of mutations in different loci of the CaM structure to preferentially affect CaM's interactions with different targets and to lead in different arrhythmia phenotypes (Chattopadhyaya, R., et al. (1992) Journal of molecular biology 228:1177-1192; Maximciuc, A. A., et al. (2006) Structure 14:1547-1556; Xia, C., et al. (2009) The J Biol Chem 284:30708-30717; Kim, E. Y., et al. (2010) The EMBO journal 29:3924-3938; Tidow, H., et al. (2013) The FEBS journal 280:5551-5565).

The molding by target concept was applied to engineer target-specific CaM based therapeutic compounds. At the same time, effector promiscuity of CaM was utilized to design a new class of disease-modifying multi-target therapeutic molecules with enhanced potency at normalizing the composite Ca release refractoriness clock. For instance, it is known that hyperactivity of CaMKII contributes to multiple cardiac pathologies, including ryanopathies. Moreover CaMKII phosphorylation of RyR2 has been shown to act by abbreviating the refractoriness clock (Belevych, A. E., et al. (2012) Circ Res 110:569-577; Belevych, A. E., et al. (2013) Cardiovasc Res 98:240-247). Thus, a strategy was developed that can dually regulate RyR2 and CaMKII to normalize RyR2 refractoriness, desynchronize aberrant Ca release and thereby alleviate cardiac arrhythmia burden in CaMKII-related ryanopathies. The universal applicability of this therapeutic approach is appealing. Specifically, gene replacement of CASQ has been effectively used to treat CASQ-related CPVT (Denegri, M., et al. (2012) Circ Res 110:663-668; Denegri, M., et al. (2014) Circulation 129:2673-2681). However, this approach is limited only to a few patients with this pathology. TCaMs can provide a broad and general strategy to target more common arrhythmias associated with genetic and acquired defects in RyR2.

Mutations in CaM result in Ca-dependent triggered arrhythmias (i.e. CPVT) similar to that caused by mutations in the components of the cardiac RyR2 complex, including RyR2, CASQ2 and Triadin (Hwang, H. S., et al. (2014) Circ Res 114:1114-1124; Nyegaard, M., et al. (2012) Am J Hum Genet 91:703-712). It has been reported that the genesis of Ca-dependent arrhythmias associated with mutations in CASQ2 involves shortened Ca release refractoriness that in turn results in aberrant diastolic Ca release (Brunello, L., et al. (2013) Proc Natl Acad Sci USA 110:10312-10317; Kornyeyev, D., et al. (2012) J Mol Cell Cardiol 52:21-31; Loaiza, R., et al. (2013) Circ Res 112:298-308). Experiments were conducted to determine whether mutations in CaM that result in Ca-dependent triggered arrhythmias (CPVT-CaMs) do so through a similar mechanism i.e. shortened refractoriness.

Figure 3A:
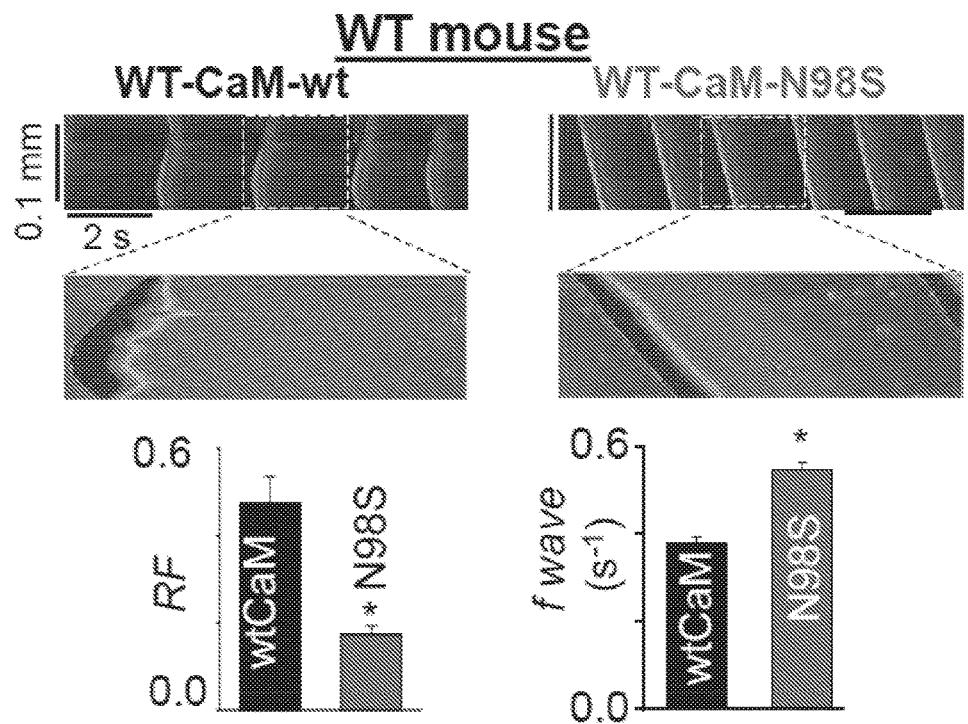
FIGS. 3A to 3C show the effects of CPVT CaM N98S and N54I on myocyte Ca handling and Ca exchange kinetics of CaM-RyR2 complex.
Figure 3B:
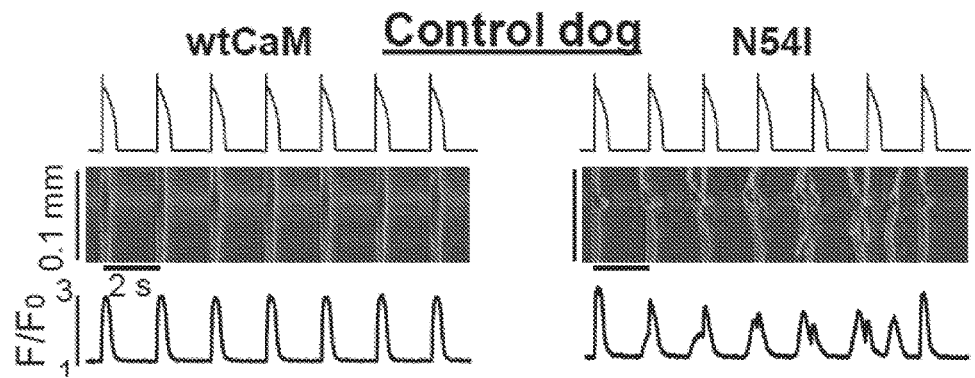

The effects of CPVT-CaMs on Ca waves and sparks was examined in saponin-permeabilized murine cardiomyocytes. Similar to previously observed effects of CPVT mutations in CASQ2 and RyR2 (Terentyev, D., et al. (2006) Circ Res 98:1151-1158; Xu, X., et al. (2010) Biochem Biophys Res Commun 394:660-666) application of CPVT-CaM N98S26 (100 nM) to the permeabilized cells increased the frequency of Ca waves and sparks compared to wild type (wt) CaM (100 nM) (FIG. 3A). To directly assess the effects of CPVT-CaM on Ca release refractoriness, the latency of Ca sparks (i.e., Ca spark restitution) following a global cellular Ca release via a Ca wave was determined. CPVT-CaM N98S (100 nM) significantly accelerated Ca spark restitution compared to wt CaM (100 nM) (FIG. 3A). Thus, CPVT-CaM shortened Ca release refractoriness in a manner similar to the action of CASQ2-associated CPVT. The aforementioned findings were confirmed in patch-clamped canine myocytes, where intracellular application of the CPVT-CaM, N54I (Hwang, H. S., et al. (2014) Circ Res 114:1114-1124; Yin, G., et al. (2014) J Am Heart Assoc 3:e000996), significantly increased the frequency of spontaneous Ca waves relative to wt CaM (FIG. 3B).

Figure 3C:
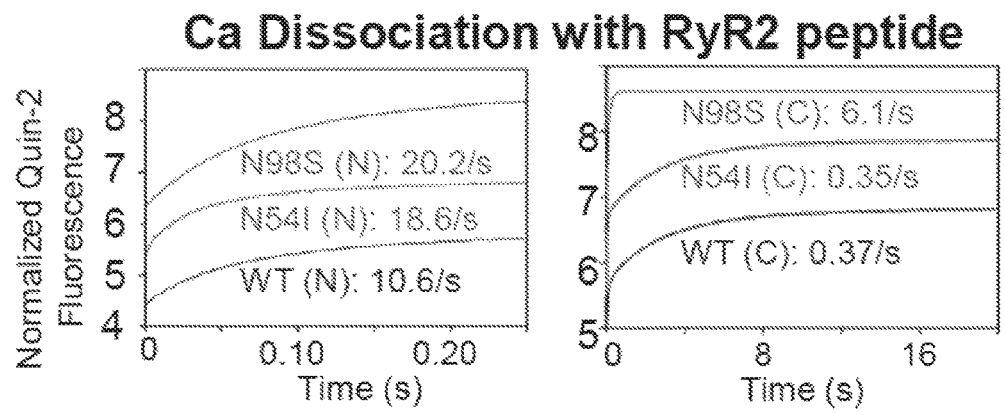

The effects of CPVT-CaMs on the Ca binding and exchange properties of CaM in the presence of the human RyR2 CaM binding peptide were also examined. In vitro Ca binding assays revealed that the N-terminal Ca binding of the CaM-RyR2 complex was reduced by CPVT-CaMs (N98S and N54I), as evidenced by a twofold acceleration in Ca disassociation (FIG. 3C). This result shows that the N-terminal rate of Ca dissociation from the CaM-RyR2 complex contributes to the regulation of the RyR2 refractory period by CaM (FIG. 2). Taken together, these experiments suggest that CPVT CaMs shorten Ca signaling refractoriness and cause cellular arrhythmogenesis in a manner similar to that observed with other genetic forms of CPVT.

Figure 4A:
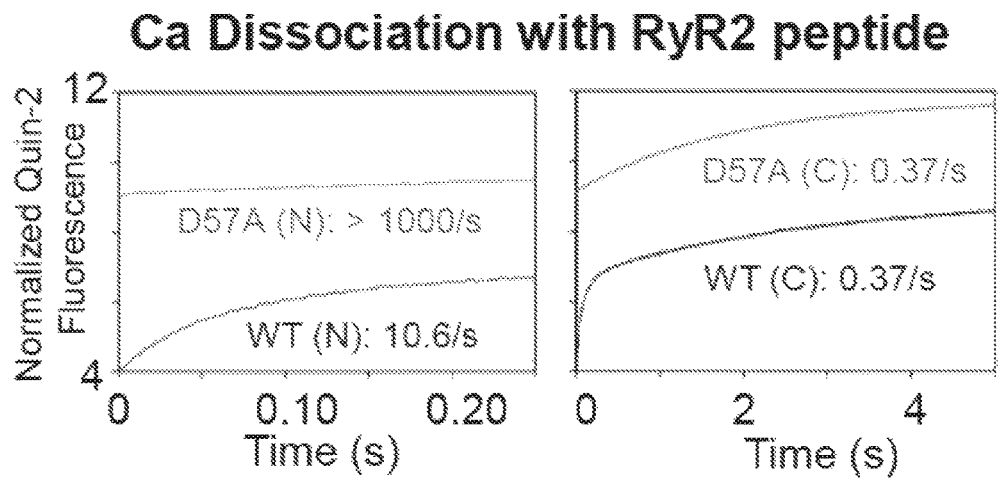
FIGS. 4A and 4B show CaM with reduced RyR2 inhibitory capability (D57A) in WT myocytes.
Figure 4B:
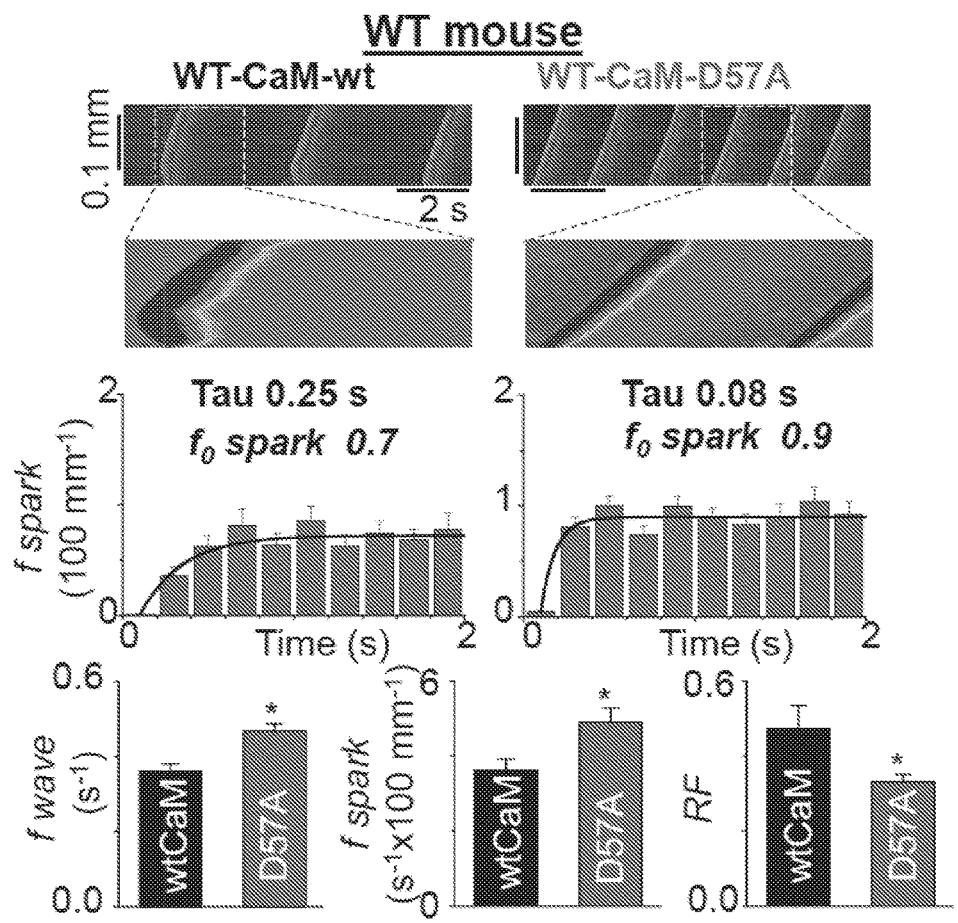
Figure 5:
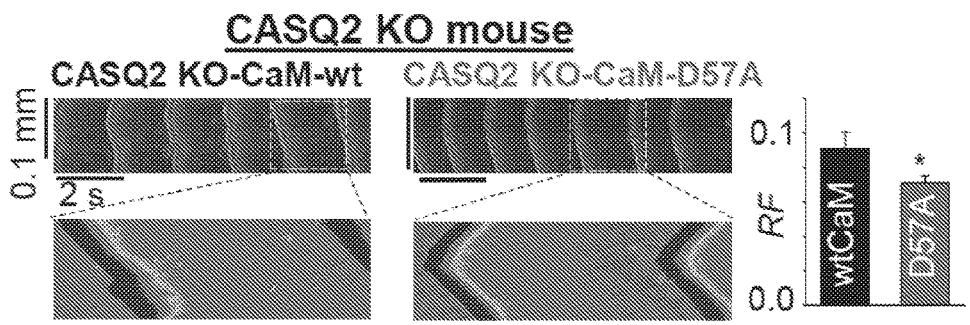
FIG. 5 shows CaM with reduced RyR2 inhibitory capability (D57A) in CASQ2 KO myocytes. Note the further reduction of Ca release refractoriness (RF).

CaM appears to mediate Ca-dependent inactivation of RyR216 (Balshaw, D. M., et al. (2001) J Biol Chem 276:20144-20153; Yang, Y., et al. (2014) Circ Res 114:295-306). As suggested above, this effect on RyR2 refractoriness is rather similar to that elicited by intra-SR luminal Ca through CASQ2 (store-dependent deactivation) (Radwanski, P. B., et al. (2013) J Mol Cell Cardiol 58:77-83, Brunello, L., et al. (2013) Proc Natl Acad Sci USA 110:10312-10317; Stevens, S. C., et al. (2009) J Physiol 587:4863-4872). Here the possibility that these two mechanisms (i.e. cytosolic Ca/CaM and luminal Ca/CASQ2) contribute in tandem to overall Ca release refractoriness was examined. To this end, a CaM construct (CaM D57A) with reduced ability to bind Ca at its N-terminus was engineered. CaM-D57A drastically decreased N-terminal Ca sensitivity (95 fold reduction) by greatly accelerating Ca dissociation from the N-terminal domain of the CaM-RyR2 complex (albeit with negligible effects on C-terminal Ca dissociation) (FIG. 4A). The functional effects of CaM-D57A was assessed in permeabilized WT or CASQ2 KO murine cardiomyocytes. As expected, the addition of CaM-D57A (100 nM) to WT myocytes increased the frequency of Ca waves and sparks relative to wt CaM (FIG. 4B), while abbreviating Ca sparks refractoriness (FIG. 4B). Importantly, CaM-D57A (100 nM) further increased Ca wave frequency and abbreviated Ca spark refractoriness in CASQ2 KO cells (FIG. 5). Collectively, these results suggest that both CaM and CASQ2 contribute to regulation of RyR2 functional activity. Therefore, these two complementary regulatory mechanisms operate in tandem by contributing to a common Ca signaling refractoriness mechanism i.e. composite refractoriness clock (FIG. 1).

Figure 6A:
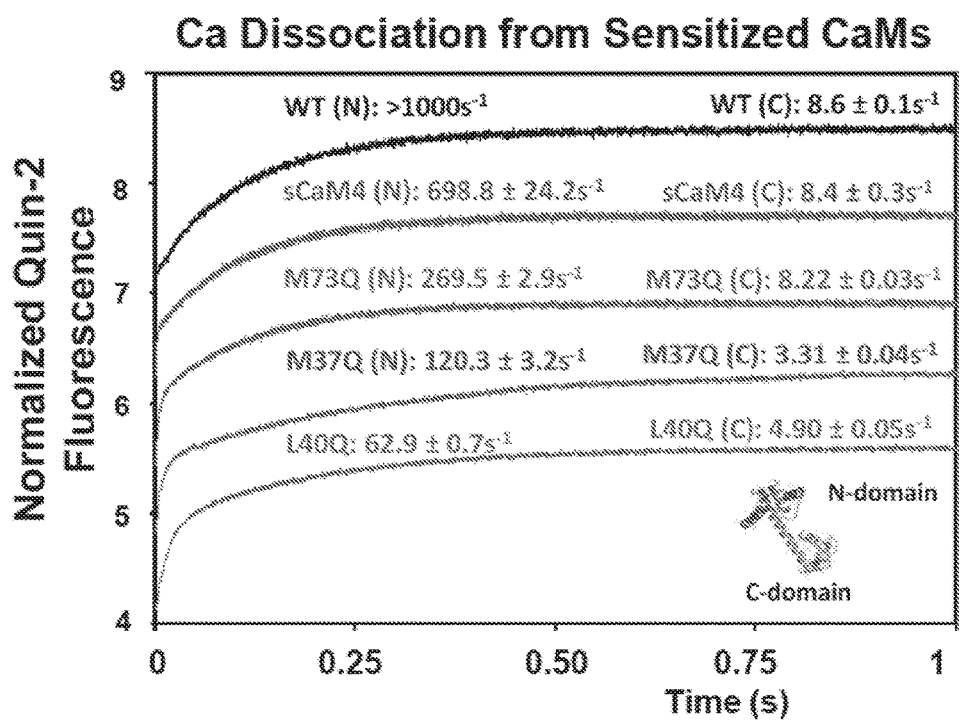
FIGS. 6A to 6B show properties of engineered TCaMs with greater than 10-fold slower N-terminal Ca dissociation rates (FIG. 6A), that can bind the human RyR2 CaM binding domain with ~5 to 10 fold higher affinity than the CPVT-CaMs at diastolic Ca levels (FIG. 6B).
Figure 6B:
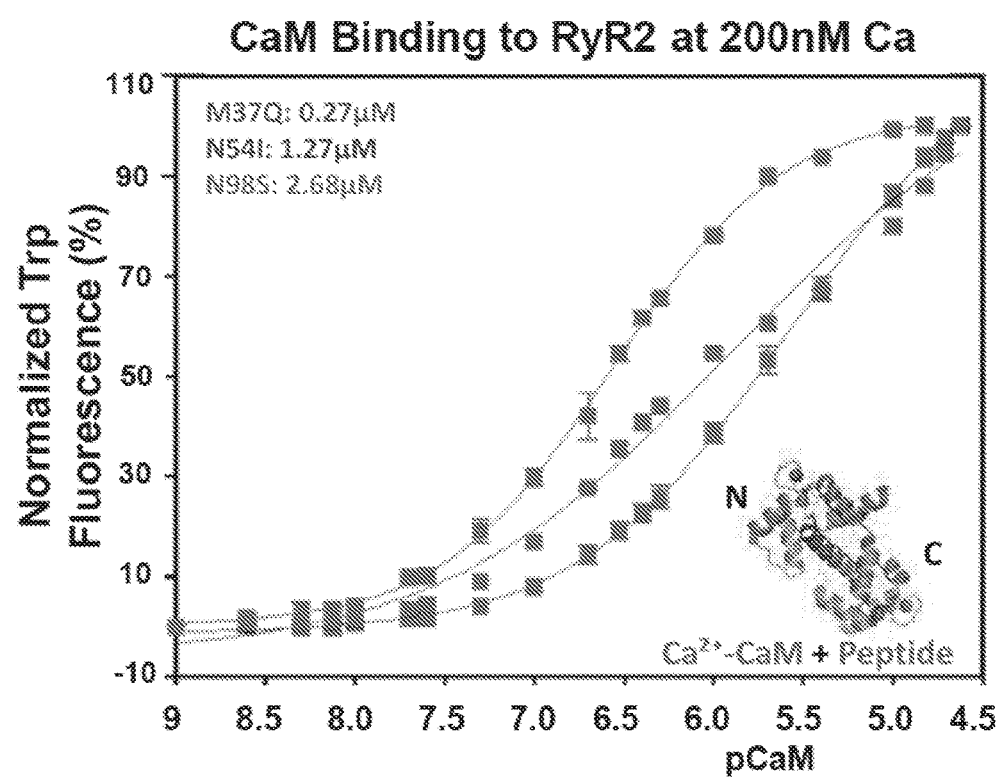

Given 1) the role of shortened refractoriness in arrhythmogenesis and 2) the ability of reduced Ca binding to the N-domain of CaM to influence the composite refractoriness clock in our preliminary studies, it was hypothesized that CaM variants with a slower N-terminal Ca dissociation rate would prolong Ca release refractoriness, i.e. "reset the refractoriness clock", and thereby reduce Ca-dependent arrhythmogenesis. To this end, therapeutic CaMs with a slower N-terminal Ca dissociation rate were engineered. FIG. 6A demonstrates that a series of CaMs can be designed with up to an order of magnitude slower N-terminal Ca dissociation rate compared to WT CaM (with negligible effects on the C-terminal Ca dissociation rate). Furthermore, at near physiological resting Ca levels in a myocyte, M37Q CaM has a 5 to 10-fold higher affinity for the human RyR2 CaM binding domain than that of the CPVT-CaMs (FIG. 6B). Considering M37Q has a slower N-terminal Ca dissociation rate and binds with high affinity to the RyR2 peptide, it was hypothesized that this formulated CaM might have a therapeutic potential against CPVT. In order to make M37Q CaM even more selective for intact RyR2 the tripeptide, GSH, was added to the N-terminal of M37Q CaM. The addition of GSH to the N-terminal of CaM has been shown to enhance the binding of CaM to RyR1 and RyR2 (Fukuda, M., et al. (2014) Biochem Biophys Res Commun 448:1-7).

Figure 7A:
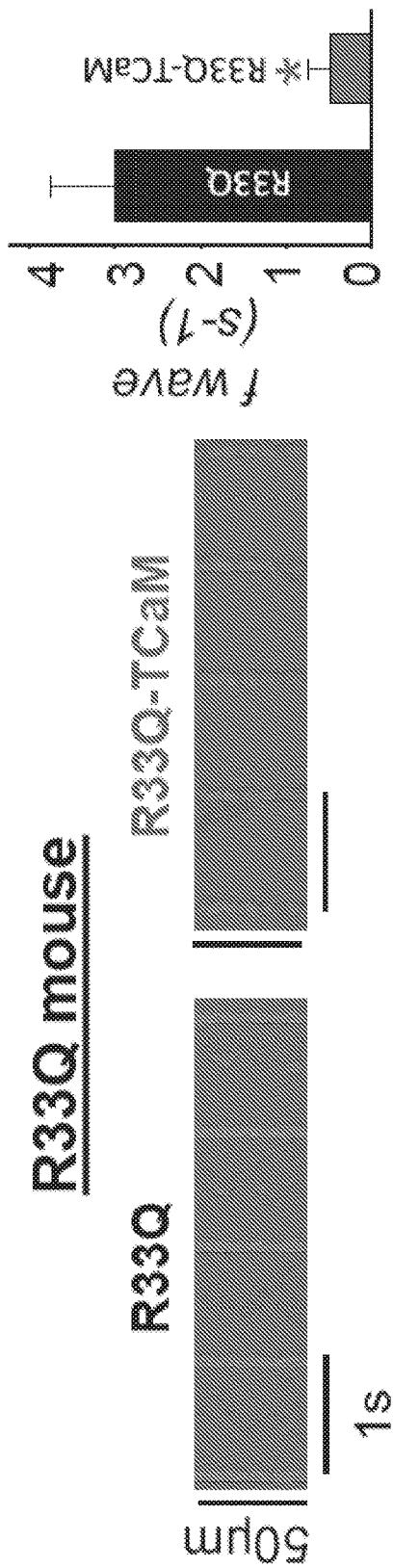
FIGS. 7A and 7B show TCaM alleviated ventricular tachycardia in vivo in CPVT mice R33Q.
Figure 7B:
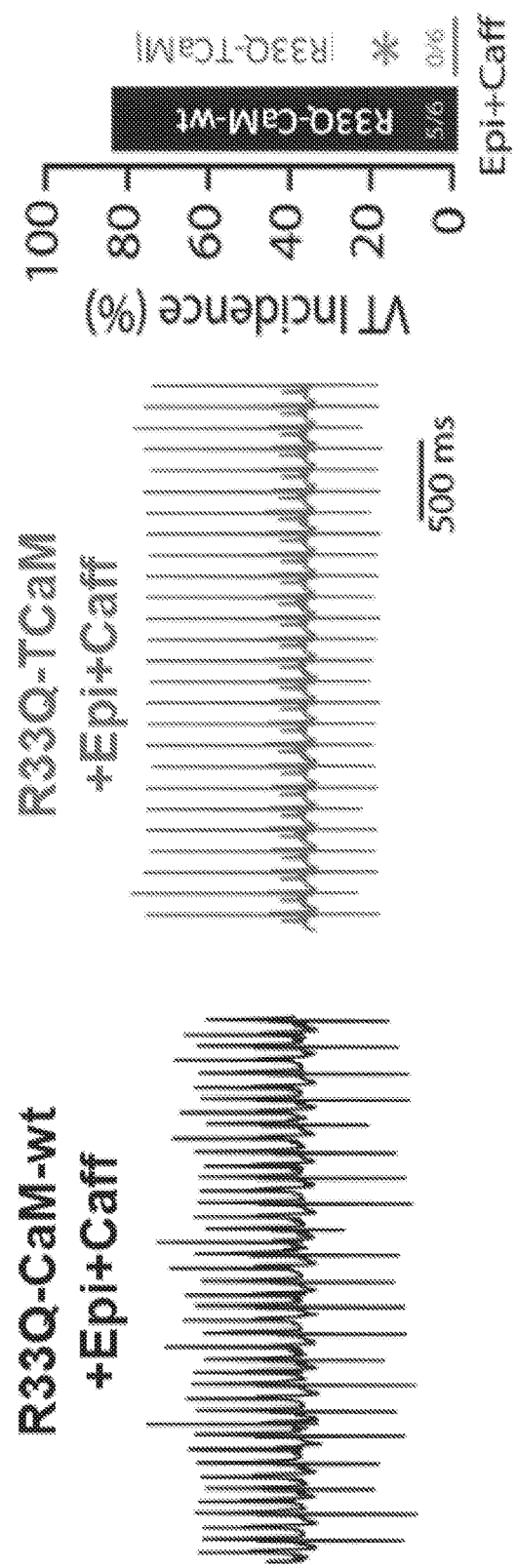
Figure 8A:
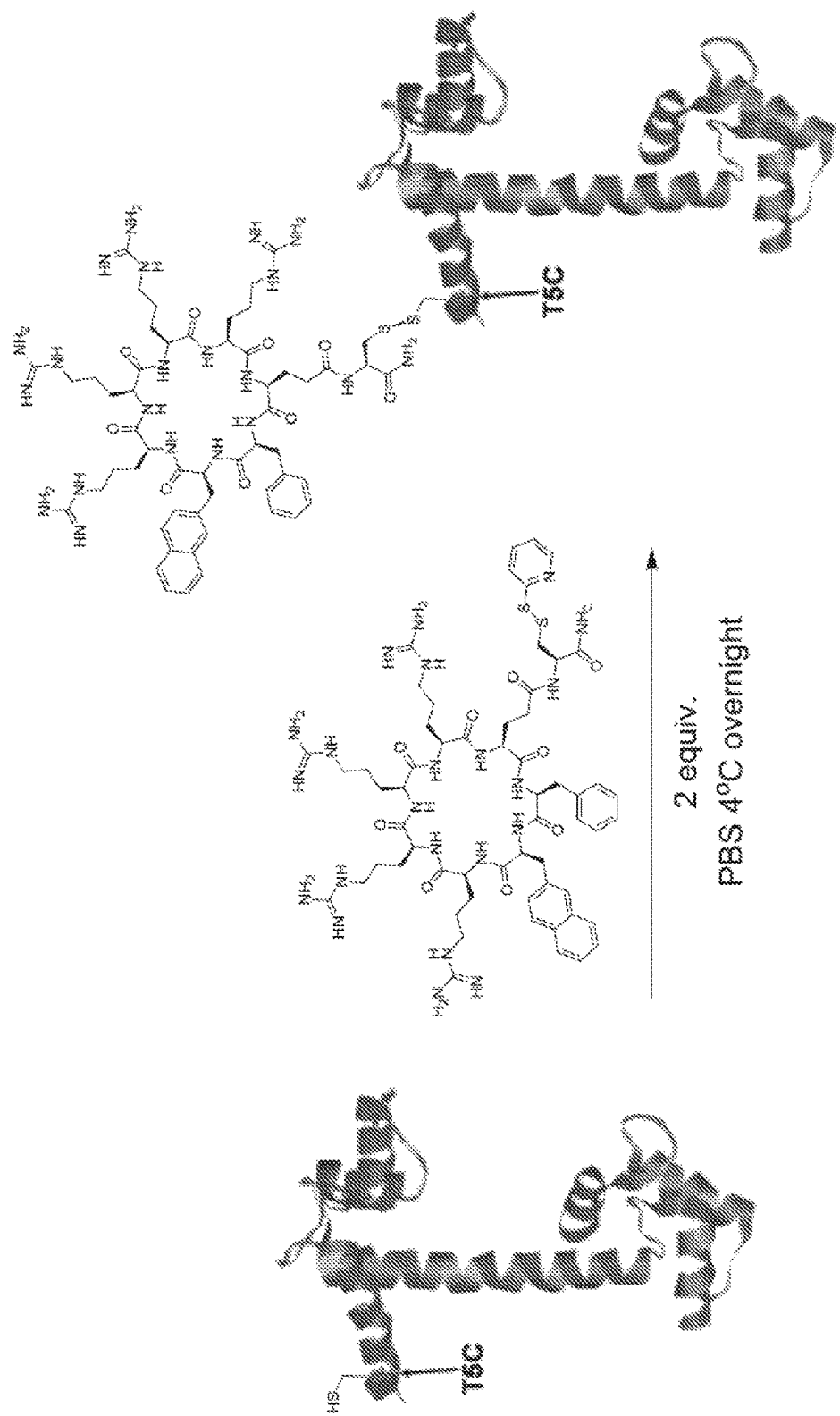
FIGS. 8A and 8B show delivery of CaM to the intact mouse ventricular myocytes using a cyclic peptide delivery system.
Figure 8B:
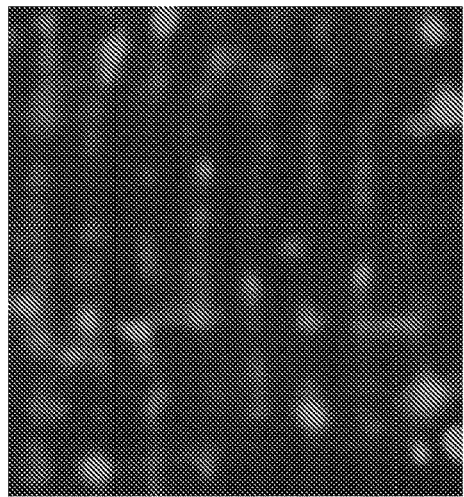
Figure 8B:
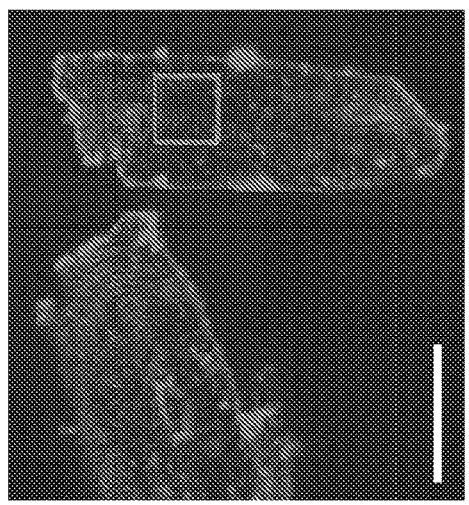
Figure 8B:
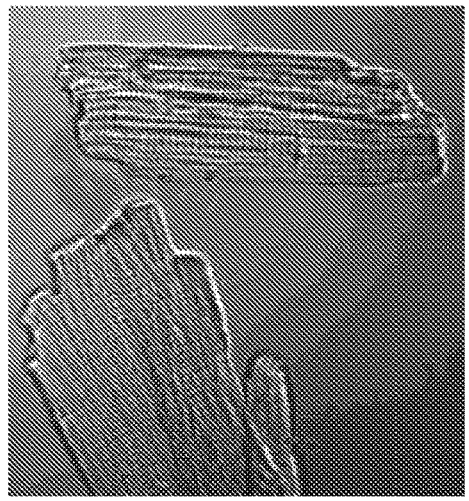

The first generation TCaM, GSH-CaM-M37Q was delivered to adult mice (12 week of age) with a cardiac calsequestrin-associated CPVT mutation (R33Q) (Rizzi, N., et al. (2008) Circ Res 103:298-306) using adeno-associated virus serotype 9 (AAV9). Greater than 60% of the heart can be transduced with AAV9 (Shettigar, V., et al. (2016) Nat Commun 7:10794). Eight weeks post-injection, confocal microscopy was performed to assess Ca handling. During catecholamine stimulation with isoproterenol (Iso; 100 nM) TCaM reduced Iso-promoted diastolic Ca release (DCR) in isolated R33Q cardiomyocytes (FIG. 7A). More importantly, when surface electrocardiograms (ECG) were performed to assess susceptibility to arrhythmias in vivo, TCaM exposure abolished ventricular tachycardia (VT) in R33Q mice undergoing epinephrine and caffeine challenge, which was not accomplished in wt CaM treated R33Q mice (FIG. 7B). Thus, these results suggest that gene transfer of TCaM by AAV9 alleviates arrhythmias in vivo, thus supporting the potential of a virally-delivered CaM-based antiarrhythmic approach as a general therapeutic avenue for management of CPVT.

Example 2

Recent work has suggested that naturally occurring mutations in the multifunctional CaM can result in CPVT (CPVT-CaM), phenotypically similar to that caused by mutations in RyR2 or the RyR2 auxiliary proteins CASQ2 and TRD (Hwang, H. S., et al. (2014) Circ Res 114:1114-1124; Nyegaard, M., et al. (2012) Am J Hum Genet 91:703-712; Sondergaard, M. T., et al. (2015) The FEBS journal 282: 803-816). Consistent with the notion that CPVT is caused by dysfunctional RyR2, initial studies with the CPVT-CaMs showed impaired RyR2 function is at the core of the disorders (Hwang, H. S., et al. (2014) Circ Res 114:1114-1124). These findings, however, lead to several critical questions. Are the mechanisms that underlie CaM-dependent CPVT modulation of RyR2 similar to other genetic forms of CPVT and whether there is any interplay between different genetic forms of CPVT mutants? Given the multifunctional nature of CaM, how can it be that the CPVT mutations in CaM appear to specifically cause RyR2 malfunction? This example examines whether arrhythmogenesis caused by CPVT-CaMs is attributable to shortened Ca release refractoriness. Furthermore, since CaM and CASQ2 effects appear to have an additive effect on RyR2 refractoriness (see FIG. 5, CASQ2 KO+CaMD57A), they may operate in tandem to compose a composite refractoriness clock, that when abbreviated—independent of the etiology—results in aberrant Ca release and cardiac arrhythmias. This example further examines whether CaM's ability to sense and respond to Ca is strongly influenced by the target it binds (Chin, D., et al. (2000) Trends Cell Biol 10:322-328). Specifically, it is proposed that since these targets do not share a common CaM binding domain, the effect of the CaM mutations will be target-specific, (i.e. "molded by target"). Resolving these issues can not only offer insight into the mechanisms responsible for CaM-related CPVT, but they can lead to the development of therapeutic CaMs to mitigate arrhythmias.

First, the impact of the CPVT-CaM mutations on the arrhythmogenic potential of cardiac myocytes is evaluated. The effects of the mutations on Ca release refractoriness as assessed by restitution of SR Ca release is tested directly. The mechanisms of action of CaM mutations are further defined by a combination of in vitro CaM-Ca binding assays and single RyR2 recordings. Next, the specificity of the CaM mutants for RyR2s are tested in the cardiac myocyte by also determining the potential effects of the CaMs on Cav1.2, Nav1.5, calcineurin (CaN) and CaMKII activities as previously described (Hwang, H. S., et al. (2014) Circ Res 114:1114-1124; Wang, H., et al. (2009) J Mol Cell Cardiol 47:304-314; Liu, Q., et al. (2006) Mol Cell Biol 26:3785-3797; Hund, T. J., et al. (2008) J Mol Cell Cardiol 45:420-428; Glynn, P., et al. (2015) Circulation 132:567-577; Radwanski, P. B., et al. (2014) Cardiovasc Res 106:143-152). The molecular mechanisms underlying the specificity of action of CPVT-CaMs on RyR2 are defined using a combination of in vitro CaM-Ca-RyR2 binding assays and CaM binding experiments in myocytes. Finally, modes of summation of the regulatory influences of CaM with those of CASQ2 or RyR2 are examined to determine whether and how these parallel mechanisms of control contribute to the composite refractoriness clock on SR Ca release at the myocyte and single RyR2 levels.

CPVT-CaM mutants are expressed in bacteria and purified as previously described (Black, D. J., et al. (2000) Biochemistry 39:13831-13837). The following experimental protocols are used to determine the effects of the CPVT-CaMs on myocyte arrhythmogenic potential and Ca signaling refractoriness. In permeabilized myocytes, the effects of the CaM mutants on Ca waves and sparks (frequency, amplitude, rate, duration) are quantified as a function of the SR Ca content. CaM mutants will be applied to the internal solution at 1-300 nM (Hwang, H. S., et al. (2014) Circ Res 114:1114-1124). Refractoriness of Ca release are measured by quantifying restitution of sparks following waves as well as by measuring repetitive Ca sparks in the presence of RyR2 openers (Imperatoxin A or ryanodine) (Ramay, H. R., et al. (2011) Cardiovasc Res 91:598-605). SR Ca content is measured by caffeine or directly assayed by Fluo-5N (Belevych, A. E., et al. (2012) Circ Res 110:569-577; Stevens, S. C., et al. (2009) J Physiol 587:4863-4872; Kubalova, Z., et al. (2004) J Physiol 561:515-524; Belevych, A. E., et al. (2009) Cardiovasc Res 84:387-395; Belevych, A. E., et al. (2011) Cardiovasc Res 90:493-502). Experiments in intact and patch-clamped myocytes allows for examination of the effects of CaMs on release properties more accurately and under conditions closer to "physiological". For CaM delivery into intact cardiomyocytes a cyclic peptide delivery system is used (Qian, Z., et al. (2013) ACS Chem Biol 8:423-431). The feasibility of this delivery approach in cardiac myocytes is illustrated in FIG. 8. In intact and patch-clamped paced myocytes (0.5-4 Hz) the effects of CaMs on basic properties of systolic Ca transients (amplitude, time-to-peak, decay), diastolic Ca waves (frequency, amplitude, length, rate), sparks (frequency, time to peak, decay time) and SR Ca content are determined. This is accomplished under control conditions and during perfusion of Iso (30-1000 nM). The effects of CaMs on excitation-contraction coupling gain (CaT amplitude/ICa) and fractional release (CaT amplitude/SR Ca content) are also determined. The effects of the CaMs on Ca release refractoriness are measured as restitution of sparks and by two pulse restitution experiments (Belevych, A. E., et al. (2012) Circ Res 110:569-577; Brunello, L., et al. (2013) Proc Natl Acad Sci USA 110:10312-10317; Liu, B., et al. (2015) Cardiovasc Res 108:299-311). CaM mutants linked only to CPVT (N98S, N54I), as well as CaM mutations linked to the mixed CPVT-LQT phenotype in patients (D132E, Q136P) are tested to determine if shortened refractoriness is a common feature between "pure" and mixed CPVT mutations. The specific role of shortened Ca release refractoriness in arrhythmogenesis is further assessed by testing the effects of LQT-CaM mutations (D96V, D130G and F142L) with the same functional assays.

The N-terminal rate of Ca dissociation from the CaM-RyR2 complex can contribute to the regulation of the refractory period of RyR2 by CaM. To test this, the steady-state Ca binding affinities of the CPVT-CaMs as well as the Ca association and dissociation rates of Ca binding are defined in vitro (Liu, B., et al. (2012) J Biol Chem 287: 20027-20036; Tikunova, S. B., et al. (2010) Biochemistry 49:1975-1984; Black, D. J., et al. (2000) Biochemistry 39:13831-13837; Van Lierop, J. E., et al. (2002) J Biol Chem 277:6550-6558). These Ca binding experiments are carried out either in the presence or the absence of the peptide representing the CaM binding domain of human RyR2 (RSKKAVWHKLLSKQRKRAVVACFRMAPLYNL; amino acids 3576-3606; SEQ ID NO:11). This is important considering: 1) binding of CaM to RyR2 increases Ca binding of CaM and 2) altering CaM's Ca binding can alter CaM binding to RyR2 (FIG. 6). Binding of the different CaM variants to RyR2 is further verified in permeabilized myocytes.

Next, the effects of the CPVT-CaMs on RyR2 functional activity is directly examined by single RyR2 recordings in lipid bilayers. In these experiments (Gyorke, I., et al. (2004) Biophys J 86:2121-2128; Terentyev, D., et al. (2005) Circulation research 96:651-658; Lukyanenko, V., et al. (1996) Pflugers Arch 432:1047-1054; Terentyev, D., et al. (2008) Circ Res 103:1466-1472), the effects of the CaM mutants are determined on RyR2 gating parameters (Po, open/closed times, conductance as a function of cytosolic and luminal [Ca]). the specific role of each domain of CaM's Ca/CaM/RyR2 binding properties on RyR2 activity are determined as functions of cytosolic and luminal Ca. Correlating the biochemical properties of the CaMs with their functional effects on RyR2 can provide further insights into the mechanisms of modulation of RyR2 by CaM (i.e. changing cytosolic or luminal Ca sensitivities or directly inhibiting RyR2).

Figure 9A:
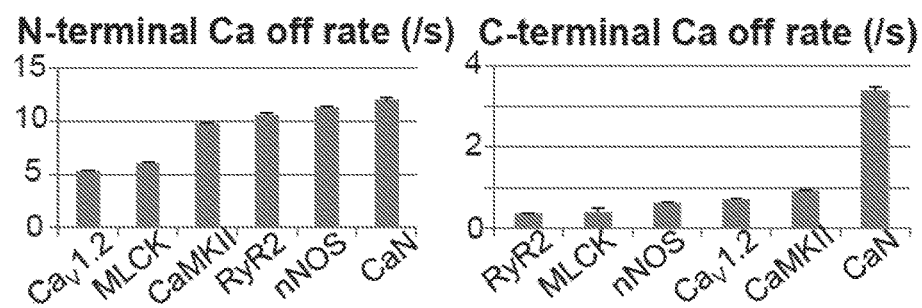
FIGS. 9A and 9B show ligand "molding by target" mechanism for specificity of multifunctional CaM.

CaM is a universal mediator of Ca signaling. The discovery that mutations in CaM can lead to CPVT, a form of arrhythmia specifically linked to RyR2 dysfunction, suggests that CaM modulation of RyR2's cytosolic targets can be selective. Moreover analysis of various CaM mutations, ranging from CPVT to long QT, can provide clues to the mechanisms of its specificity and facilitate the design of therapeutic CaMs for the treatment of ryanopathies. Two potentially complementary hypotheses for the arrhythmogenic selectivity of CaM mutations are tested: 1) the CPVT mutations enhance the binding affinity of CaM to RyR2 compared to other targets; and/or 2) due to the ligand "molding-by-target" effect, the mutant CaM's Ca binding properties are specifically altered by RyR2 binding (potentially leading to the aberrant RyR2 function and CPVT), but not by other non-selective target binding. To test these hypotheses, in vitro Ca and target-peptide binding and kinetic experiments are performed with WT and mutant CaMs in the presence and absence of peptides representing CaM binding domains of several key CaM target proteins including RyR2, CaV1.2, NOS1, CaN and CaMKII. In particular the Ca sensitivity and kinetics of WT and CPVT CaMs are compared in the presence and absence of these different CaM binding target peptides (FIG. 9). In addition CaM binding experiments are performed in permeabilized myocytes and RyR2 preparations using fluorescently labeled CaM with either single site labels or FRET pairs (Guo, T., et al. (2011) Biophysical journal 101:2170-2177; Terentyev, D., et al. (2008) Biophys J 95:2037-2048; Lukyanenko, V., et al. (2001) Biophys J 81:785-798).

Considering: 1) the similarities of CPVT phenotypes caused by mutations in CaM, CASQ2 and RyR2; and 2) that CaM is well suited to control RyR2 refractoriness via Ca-dependent inhibition of RyR245; it is proposed that cytosolic Ca and CaM control SR Ca release in a similar manner to luminal Ca-CASQ2 by facilitating RyR2 refractoriness. In this example it is hypothesized that multiple parallel pathways, including luminal and cytosolic regulation by CASQ2 and CaM respectively, as well as modifications to the RyR2 channel itself, contribute to the composite refractoriness clock (FIG. 1). To test this concept, the summation of the aforementioned functional influences to collectively affect refractoriness and aberrant Ca release are examined. In these experiments myocytes derived from WT and CASQ2 KO mice containing wt or CPVT mutant CaMs are used. As described above, Ca release refractoriness is assessed by measuring restitution of Ca transient and spark recovery under baseline conditions and during catecholamine challenge (Iso). This data then are correlated with myocyte arrhythmogenic potential (frequency of Ca waves, DADs and triggered action potentials [tAPs]). In order to determine whether and how these influences (cytosolic and luminal) interact with modulatory action of RyR2 phosphorylation at the level of RyR2 refractoriness, similar experiments are performed in myocytes obtained from RyR2 knockin mice constitutively dephosphorylated at Ser2814 (S2814A) and double mutant CASQ2KO-RyR2S2814A mice. By comparing the refractoriness in different groups whether and how these influences (cytosolic and luminal) affect RyR2 refractoriness and cellular arrhythmogenesis is assessed.

Figure 9B:
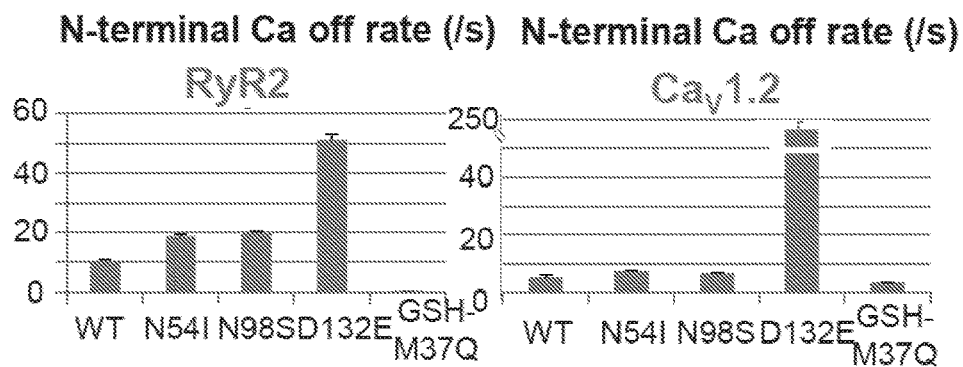

These studies directly test the hypothesis that CPVT-CaM mutations act through compromising RyR2 Ca signaling refractoriness. Results suggest that CPVT-CaM mutations indeed shorten refractoriness in permeabilized cells, but further studies can confirm and define the effects of mutant CaMs on SR Ca handling and arrhythmogenesis in myocytes. Furthermore, the specific mechanisms behind the altered refractoriness are determined: altered luminal Ca sensitivity, overall inhibition, or accelerated Ca dissociation rate from CaM. Experiments suggest that an accelerated Ca dissociation rate from the CaM-RyR2 complex contributes to the shortened refractoriness in the case of at least two CPVT-CaMs (i.e. N98S and N54I; FIG. 3). Alternatively, it is possible that different mechanisms contribute to shortened refractoriness in the case of different CPVT-CaMs. Mechanistic studies underpinning the specificity of CPVT-CaMs can provide insights into CaM-dependent arrhythmias and improve knowledge of CaM signaling in general. Functional specificity of CPVT-CaMs with regard to modulation of RyR2 can be mediated by a "molding-by-target" mechanism, which is supported by pilot studies showing that: 1)

the Ca dissociation rate from CaM is target-dependent (FIG. 9A) and 2) CPVT-CaMs accelerated the rate of Ca dissociation from CaM only in the presence of RyR2 peptide, but not in the presence of Cav1.2 peptide (FIG. 9B). Additionally, that refractoriness/stability of CICR can be determined by an assortment of parallel mechanisms residing at both the cytosolic and luminal sides of RyR2, as well as within the channel itself. Thus, there can be an additive effect from CPVT mutations of CASQ2, CaM and RyR2. Experiments demonstrate that the functional effects of CASQ2 and CaM on Ca signaling refractoriness were indeed additive (FIG. 5).

Together these mechanistic studies of CPVT-CaM not only provide insight into CaM-dependent arrhythmias, but also provide a foundation for development of RyR2 specific therapeutic CaMs for the treatment of ryanopathies (FIG. 7).

Example 3

Genetic and acquired defects in RyR2 are thought to underlie a spectrum of cardiac diseases ranging from arrhythmias to HF (i.e. ryanopathies). Although RyR2 is considered to be a logical target for the treatment of these diseases, effective therapies based on normalization of RyR2 function is lacking. CaM is a particularly promising target, as it can be rationally engineered to modulate RyR2 refractoriness (FIG. 4, 5, 7). Moreover, engineering "therapeutic" CaM (TCaM) has the added benefit of also targeting additional Ca dependent pathways. For instance, it is known that the hyperactivity of CaMKII contributes to hyperphosphorylation of RyR2 (Mishra, S., et al. (2010) J Cardiovasc Pharmacol 56:598-603; Maier, L. S., et al. (2002) J Mol Cell Cardiol 34:919-939). This in turn results in RyR2 "leakiness," thereby precipitating arrhythmogenic diastolic Ca release. A TCaM that targets both RyR2 and CaMKII simultaneously is designed to improve stability of RyR2 and diminish CaMKII activity. Based on studies with plant CaMs, such dual target mechanism is feasible through introducing another mutation at the CaMKII binding domain of CaM (Van Lierop, J. E., et al. (2002) J Biol Chem 277:6550-6558; Lee, S. H., et al. (2000) Biochem J 350 Pt 1:299-306; Cho, M. J., et al. (1998) Biochemistry 37:15593-15597). The goal of this example is to create RyR2 specific and RyR2-CaMKII dual targeting TCaMs to maximize the beneficial effects and meanwhile avoid adverse off-target effects of current pharmaceuticals.

Therapeutic CaMs (TCaMs) that bind either to RyR2 or to both RyR2 and CaMKII are designed and tested in order to prolong RyR2 refractoriness and increase Ca signaling stability. Promising CaM variants are further studied using in vivo viral transfection (Shettigar, V., et al. (2016) Nat Commun 7:10794). High-resolution confocal imaging of ventricular tissue is used to investigate the impact of such an approach with TCaMs on the synchronization of aberrant diastolic Ca release, as well as the coupling of such release at 1) the multi-cellular level and 2) on extrasystolic electrical depolarization in tissue. The relationship between viral transfection efficiency/homogeneity, desynchronization of aberrant Ca release and inhibition of triggered action potentials (tAPs) are evaluated in intact muscle preparations (trabeculae) in order to better understand the factors accounting for the efficacy of viral-delivery-based gene antiarrhythmic therapy. Furthermore, in vivo TCaM efficacy in the treatment of two genetic forms of CPVT, a CASQ2-mediated (CASQ2KO or R33Q) or RyR2-mediated (RyR2-V2475F) is assessed (Loaiza, R., et al. (2013) Circ Res 112:298-308; Rizzi, N., et al. (2008) Circ Res 103:298-306; Knollmann, B. C., et al. (2006) J Clin Invest 116:2510-2520). Finally, the translational applicability of these findings in mice is tested to Ca signaling stability reserve in canines. Furthermore, the utility of the aberrant diastolic Ca release desynchronization effect of TCaMs are examined in a clinically relevant canine model of acquired ryanopathy, i.e. chronic HF. Notably, based on the significant post-translational modification of RyR2 by CaMKII, this model serves as an ideal medium for testing the dual-acting TCaM.

In some cases, an effective therapeutic CaM can: 1) bind to RyR2; 2) alter RyR2 function by increasing the Ca signaling refractory period and increasing the stability reserve of Ca release; and 3) be selective for RyR2 without adversely affecting other important CaM targets in the heart (unless specifically designed to do so). The following main strategies are used to design such therapeutic CaMs. The N-terminus of CaM is mutated to slow Ca dissociation and thereby enhance Ca release refractoriness [as the CPVT CaMs all exhibit accelerated N-terminal Ca dissociation (see FIGS. 3, 6 & 9)]. Based on the structure of the RyR1 peptide bound to CaM, CaM mutants are engineered, especially in the N-terminal domain (where most of the CPVT mutations are clustered) that modulate the binding interface and variants that specifically improve RyR2 function are screened. All the TCaM variants can contain the N-terminal GSH extension that has been shown to increase CaM's binding affinity to RyR2 in order to enhance the target-selectivity of the TCaMs (Fukuda, M., et al. (2014) Biochem Biophys Res Commun 448:1-7). The Ca binding of TCaMs and their dependence on association with RyR2 and other targets (Cav1.2, Nav1.5, NOS1, and CaMKII) are determined by in vitro assays as described in Example 2. The functional effect of potential TCaMs are further examined by single RyR2 recordings, as well as by examining the properties of Ca release (Ca sparks, waves, EC gain) in permeabilized and patch-clamped myocytes derived from WT and CPVT mice (CASQ2KO or R33Q, and RyR2-V2475F) as described in Example 2. The specificity of the effects of prospective TCaMs on RyR2-mediated release are further tested by assaying the function of other targets (ICa, INa and CaMKII activity) as described in Example 2.

Figure 10A:
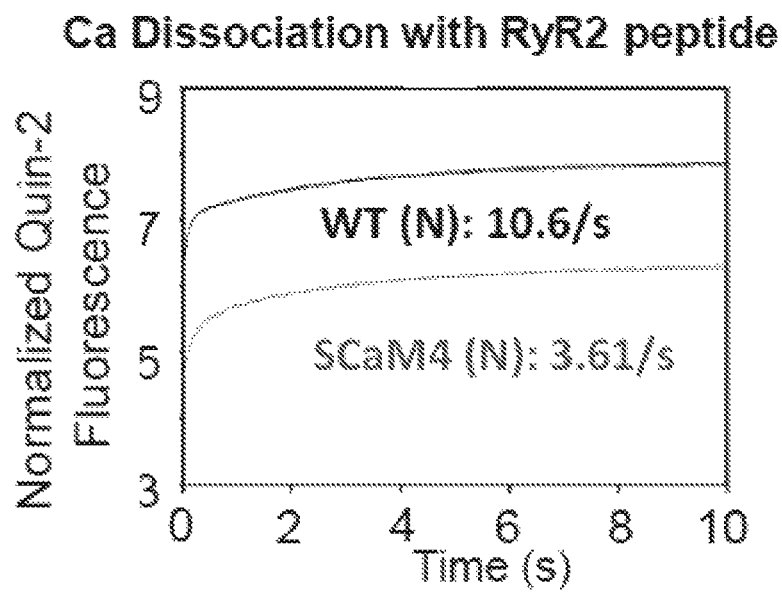
FIGS. 10A and 10B show SCaM4 slowed Ca dissociation rate from N-terminus of CaM-RyR2 (FIG. 10A), and reduced f wave in intact myocytes isolated from R33Q mice (FIG. 10B).
Figure 10B:
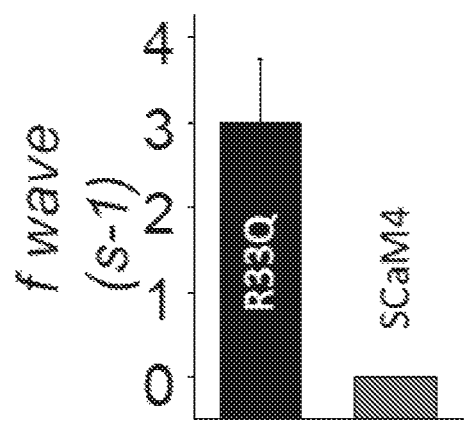

A large body of work has accumulated which suggests that CaMKII phosphorylation of RyR2 (at S2814) results in Ca-dependent arrhythmia (Pereira, L., et al. (2013) Circulation 127:913-922; Ather, S., et al. (2013) Heart Rhythm 10:592-599; DeGrande, S., et al. (2012) Heart Rhythm 9:2034-2041). Furthermore, pharmacological or genetic prevention of S2814 phosphorylation alleviates arrhythmias by slowing RyR2 refractoriness. Therefore dual target TCaMs that will prolong RyR2 refractoriness by targeting both RyR2 and CaMKII are developed. The key mutations for inhibiting CaMKII activity can be mapped by comparative studies on human CaM and soybean CaM4 (Van Lierop, J. E., et al. (2002) J Biol Chem 277:6550-6558; Lee, S. H., et al. (2000) Biochem J 350 Pt 1:299-306; Kondo, R., et al. (1999) J Biol Chem 274:36213-36218). While human CaM has only one isoform and is extremely conserved across the mammalian species, numerous plant CaM isoforms are expressed and exert target specific functions (Lee, S. H., et al. (2000) Biochem J 350 Pt 1:299-306; Cho, M. J., et al. (1998) Biochemistry 37:15593-15597). One of the enzymes that a plant CaM drastically impairs functionally, while maintaining normal regulatory function of the other targets, is CaMKII (Lee, S. H., et al. (2000) Biochem J 350 Pt 1:299-306). the minimal mutations required in CaM to in essence shut down CaMKII function are determined (Van Lierop, J. E., et al. (2002) J Biol Chem 277:6550-6558). As a first attempt to generate next generation dual targeting TCaM, soybean CaM 4 (SCaM4) that has a slower N-terminal Ca dissociation rate in the presence of the RyR2 peptide (FIG. 10A) are used to prolong RyR2 refractoriness, and also contains the amino acid modifications essential for impairing CaMKII activity (Lee, S. H., et al. (2000) Biochem J 350 Pt 1:299-306). Data suggests SCaM4 reduced waves in isolated myocytes from a mouse model of CPVT (FIG. 10B). In order to make SCaM4 more specific to RyR2 and CaMKII, GSH can be added and the minimal mutations necessary for inhibiting CaMKII function can be pinpointed (Van Lierop, J. E., et al. (2002) J Biol Chem 277:6550-6558).

Select CaMs with the most pronounced antiarrhythmic effects and best selectivity profiles are further studied using in vivo gene delivery (Shettigar, V., et al. (2016) Nat Commun 7:10794). For the in vivo viral transfection, AAV9 is used to introduce C-terminal flag-tagged TCaM constructs into the heart. AAV9 is produced in HEK293 cells and purified using an iodixanol gradient protocol (Shettigar, V., et al. (2016) Nat Commun 7:10794; Johnson, P. R., et al. (2009) Nature medicine 15:901-906). The virus titer is obtained via TaqMan (LifeTechnologies) based quantification. AAV9 (100 µl, containing $1 \times 10^{11}$ viral genomes) is injected into adult mice (12 to 14 weeks old) through the intra-thoracic cavity (Shettigar, V., et al. (2016) Nat Commun 7:10794). This straightforward technique ensures efficient and highly reproducible viral transduction specifically to the adult heart, meanwhile minimizing the risk of damaging the beating heart (Shettigar, V., et al. (2016) Nat Commun 7:10794). The virally expressed mRNA is stabilized by the woodchuck post-translational response element, increasing CaM yield. Furthermore, along with the CaM construct, the virus also expresses a separate fluorescent reporter protein, mCherry, using an internal ribosomal entry site motif (IRES) (Shettigar, V., et al. (2016) Nat Commun 7:10794). Transfection efficacy is quantified at the cellular level by mCherry fluorescence and at the protein level using the flag tag on the C-terminal domain of CaM. 50%-70% cardiac transduction is routinely observe (Shettigar, V., et al. (2016) Nat Commun 7:10794) (FIG. 11).

The therapeutic potential of these TCaMs in alleviating arrhythmias is assessed in both CASQ2- (CASQ2 KO or R33Q) or RyR2-associated (RyR2-V2475F) CPVT mice using surface ECG recordings, as well as telemetry (Liu, B., et al. (2015) Cardiovasc Res 108:299-311; Curran, J., et al. (2014) Circ Res 115:68-78), during acute catecholamine challenge (epinephrine 1.5 mg/kg and caffeine 120 mg/kg) (Radwanski, P. B., et al. (2014) Cardiovasc Res 106:143-152).

Further, the cellular and subcellular effects of AAV9-delivered TCaM on Ca handling are examined in isolated CPVT myocytes. The effect of TCaM on cellular pro-arrhythmic potential as well as refractoriness are measured as described above (see FIGS. 3 and 7).

Figures 11A, 11B, 11C, 11D:
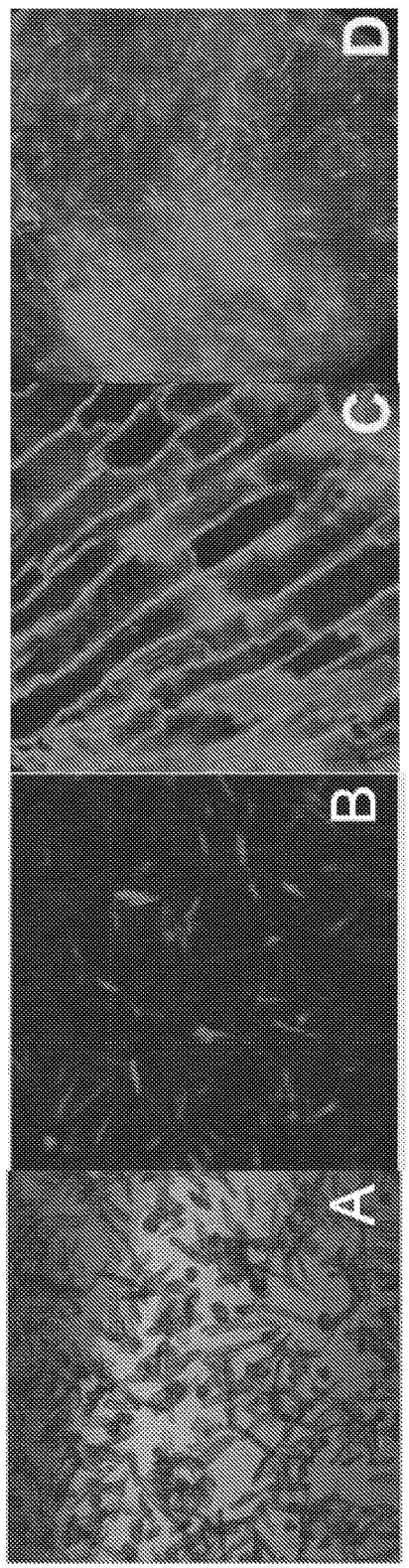
FIGS. 11A to 11D show efficacy of AAV9-mediated gene transfer to cardiac myocytes.
Figure 12A:
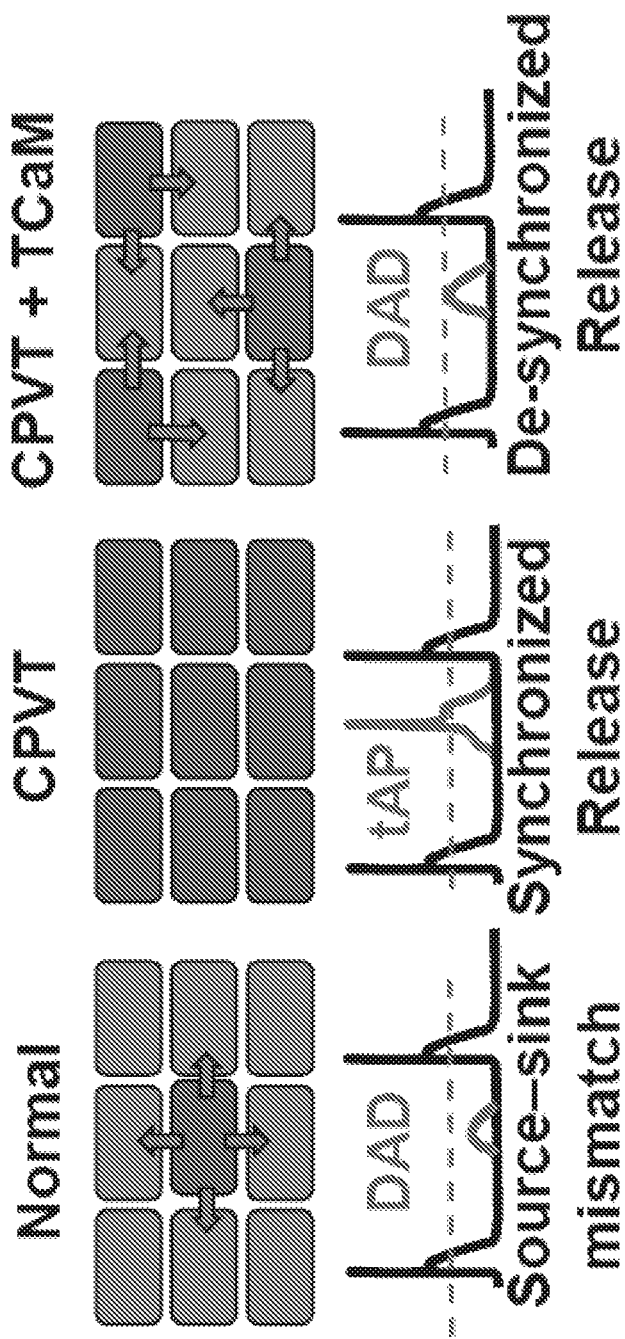
FIGS. 12A and 12B show synchronization of aberrant Ca release in CPVT and its antiarrhythmic desynchronization in cardiac tissue presented schematically (FIG. 12A) and as representative Ca (top) and Vm (bottom) images acquired in CASQ2KO mouse trabeculae (FIG. 12B).
Figure 12B:
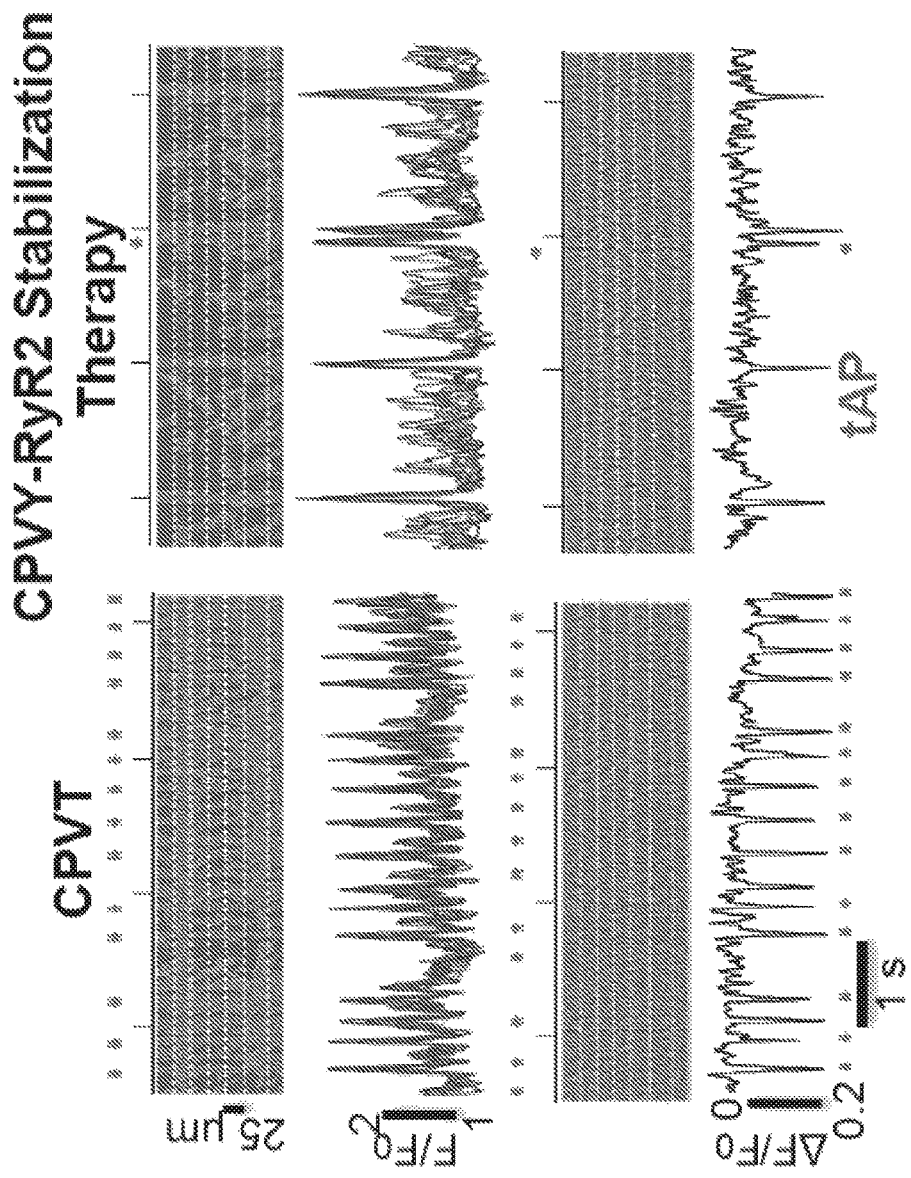
Figure 13A:
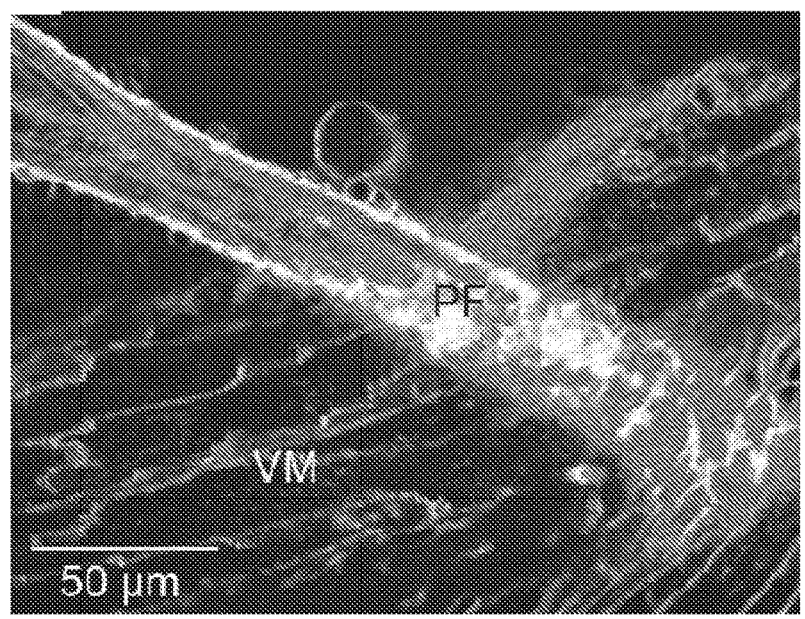
FIGS. 13A and 13B show Ca recordings in Purkinje fibers in the right ventricular wall of CASQ2KO mouse heart.
Figure 13B:
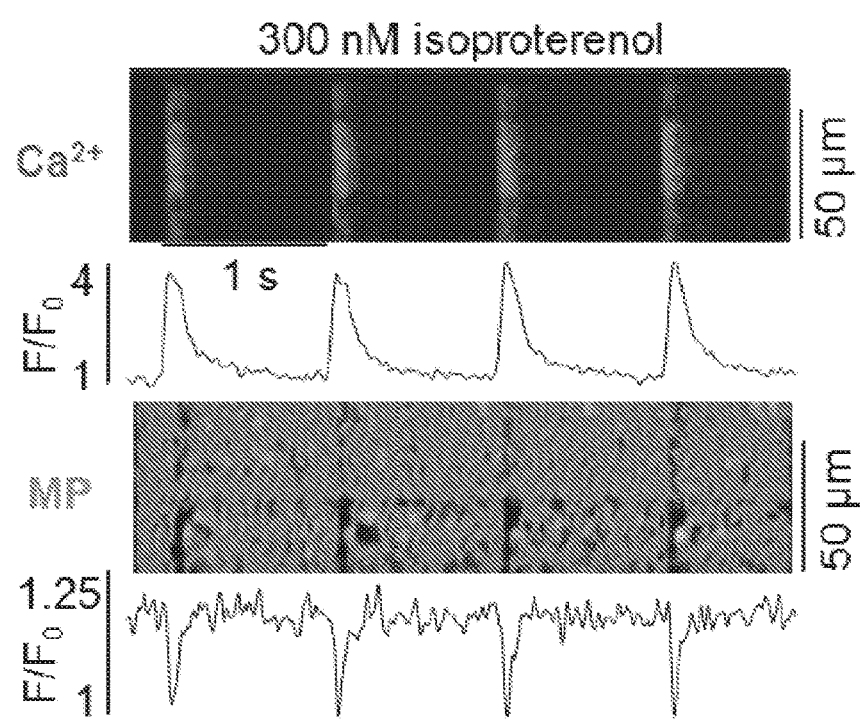

By applying confocal Ca and membrane potential imaging to multicellular preparations (trabeculae), it has been shown that in order to initiate triggered activity in the form of triggered action potentials (tAPs), aberrant Ca release has to occur synchronously across a critical mass of myocardium (Brunello, L., et al. (2013) Proc Natl Acad Sci USA 110:10312-10317; Radwanski, P. B., et al. (2014) Cardiovasc Res 106:143-152). Consistent with this concept, RyR2 stabilization therapy, with such agents as dantrolene, can potentially reduce the synchronicity of aberrant Ca release (Brunello, L., et al. (2013) Proc Natl Acad Sci USA 110: 10312-10317). Such therapeutic RyR2 stabilization, in turn may inhibit the tAPs in cardiac tissue (FIG. 12B). Therefore, the ability of TCaMs to desynchronize aberrant Ca release and inhibit tAPs is determine in trabeculae preparations isolated from CPVT mice of various etiologies (CASQ2KO or R33Q and RyR2-V2475F). Ventricular trabeculae loaded with Ca- and Vm indicators (Rhod 2, di-4-ANEPPS or di-4ANBDQBS) are stimulated (0.5-5 Hz) and Ca and Vm changes simultaneously monitored with cellular/subcellular resolution confocal imaging. To assess the pro- and anti-arrhythmogenic effects of CaM-modulated diastolic Ca release, the frequency of tAPs is related to the frequency of DCRs and to their synchronicity (i.e. SD of first latencies of DCRs) across the trabeculae. Transfection efficiency for different infection titers ($1 \times 10^{10}$ to $5 \times 10^{12}$ viral genomes) are quantified by assessing the mCherry signal. The relationship between release synchronicity and tAPs occurrence is evaluated as a function of TCaM transduction efficiency. As a positive control WT-CASQ2 viral transduction is used in CASQ2KO mice, an established antiarrhythmic strategy (Denegri, M., et al. (2012) Circ Res 110:663-668; Denegri, M., et al. (2014) Circulation 129:2673-2681). The feasibility of these experiments is illustrated in FIGS. 11B and 11C where AAV9 transduction of WT mouse results in similar transduction efficiency in trabeculae relative to the rest of the heart. These experiments allow determination of whether wt-CASQ2 and TCaMs gene transfer can de-synchronize diastolic release in the myocardium. Importantly, it has been previously suggested that triggered activity arises preferentially from the Purkinje system (Cerrone, M., et al. (2007) Circ Res 101:1039-1048; Herron, T. J., et al. (2010) Heart Rhythm 7:1122-1128; Ter Keurs, H. E., et al. (2007) Physiol Rev 87:457-506; Xie, Y., et al. (2010) Biophys J 99:1408-1415). Hence, it can be reasonably postulated that the therapeutic efficiency of wt—CASQ2 and TCaM gene transfer could be potentially due to preferential transduction of the Purkinje fibers. Therefore, as an alternative strategy, is to consider performing comparative experiments in mouse Purkinje fibers using the general approaches outlined for mouse trabeculae (Brunello, L., et al. (2013) Proc Natl Acad Sci USA 110:10312-10317; Hamamoto, T., et al. (2005) J Mol Cell Cardiol 38:561-569). The feasibility of this approach is demonstrated in FIG. 13, which shows recordings of pacing-induced-Ca transients in a Purkinje fiber from a CPVT mouse.

Figure 14A:
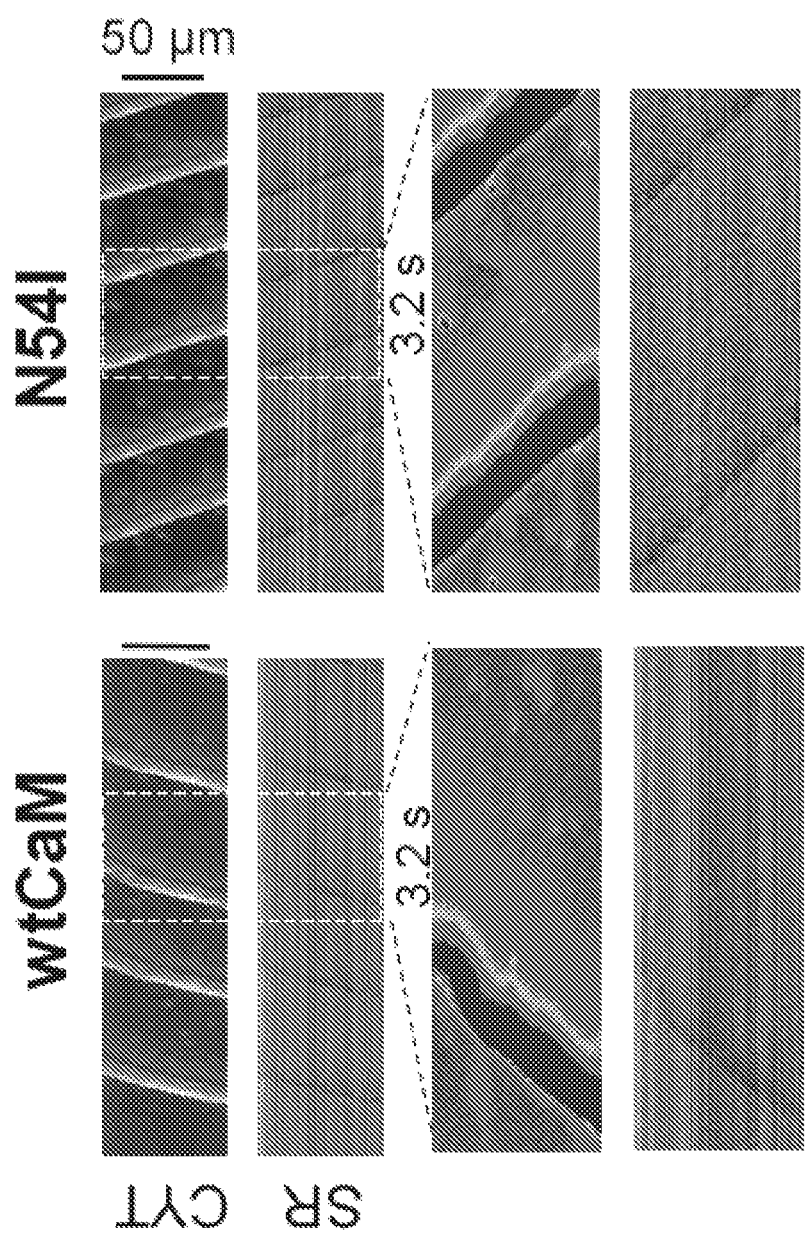
FIGS. 14A and 14B show CPVT CaM (N54I) induced diastolic Ca waves in control canine ventricular myocytes.
Figure 14B:
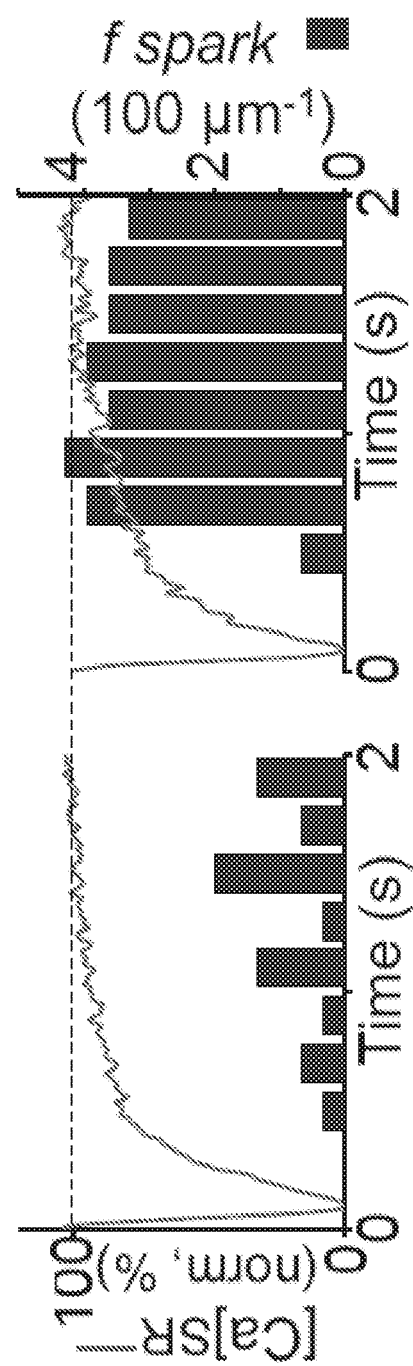

Given the similarity of underlying RyR2 pathologies in genetic and acquired ryanopathies, the ability of therapeutic CaMs to improve Ca handling in HF is also assessed. In these studies a clinically relevant canine model of chronic HF is used (Belevych, A. E., et al. (2009) Cardiovasc Res 84:387-395; Belevych, A. E., et al. (2011) Cardiovasc Res 90:493-502; Terentyev, D., et al. (2008) Circ Res 103:1466-1472; Hamamoto, T., et al. (2005) J Mol Cell Cardiol 38:561-569). First the applicability of the findings in Example 2 is examined in control canines. Then the effects of TCaMs on parameters of Ca handling in normal and HF myocytes are examined as described in Example 2 for mouse studies. Based on preliminary results, CaM is capable of abbreviating Ca release refractoriness without altered luminal regulation (FIG. 14).

These studies can lead to the development of single and dual-target therapeutic CaMs that increase Ca signaling refractoriness and improve Ca signaling stability. A TCaM (GSH-M37Q) has been successfully developed that when delivered into a CPVT mouse model (CASQ2 R33Q) through AAV9, reduced Iso-promoted DCR on the cellular level and completely abolished ventricular tachycardia in vivo. A prototype dual-target TCaM has also been developed whose stabilizing effect on Ca cycling is strengthened by binding to and inhibition of CaMKII in addition to RyR2. As a complementary strategy, other dual target CaMs that affect ion channels such as CaV1.2 and NaV channels to further help block arrhythmias are also developed. Engineered CaMs can be used to alter either a single target or a combination of additional targets to rewire CaM's activation profile in the heart to combat a plethora of cardiovascular diseases and disorders. Additionally, diastolic Ca release is highly synchronized in CPVT ventricular myocytes (FIGS. 3 and 14) and in cardiac tissue (FIG. 12) due in part to abnormally abbreviated Ca release refractoriness (Brunello, L., et al. (2013) Proc Natl Acad Sci USA 110:10312-10317; Kornyeyev, D., et al. (2012) J Mol Cell Cardiol 52:21-31). Therefore, slowing Ca release refractoriness with TCaMs can reduce the incidence and synchronicity of aberrant Ca release events on the cellular level, which will translate into reduced tAPs in tissue (FIG. 12).

Data is compared using unpaired student's t-test or one-way ANOVA when appropriate; all values are reported as means±standard deviation unless otherwise noted. P<0.05 is considered statistically significant.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising the amino acid sequence SEQ ID NO:1 having at least one mutation selected from the group consisting of F13Q, T27D, T29D, M37Q, L40Q, N61D, M72Q, and M73Q.

2. The isolated polypeptide of claim 1, wherein the polypeptide has the amino acid sequence SEQ ID NO:2.

3. The isolated polypeptide of claim 1, wherein the polypeptide is cyclized.

4. The isolated polypeptide of claim 1, further comprising an N-terminal glutathione.

* * * * *